(12) United States Patent
O'Dea et al.

(10) Patent No.: US 9,168,364 B2
(45) Date of Patent: Oct. 27, 2015

(54) TRANSFER DEVICE FOR TRANSFERRING A SUBSTANCE BETWEEN THE DEVICE AND A SUBJECT

(75) Inventors: John O'Dea, Bearna (IE); Eoin Bambury, Navan (IE)

(73) Assignee: JANISYS LIMITED, Galway (IE)

(*) Notice: Subject to any disclaimer, the term of this patent is extended or adjusted under 35 U.S.C. 154(b) by 914 days.

(21) Appl. No.: 13/127,287

(22) PCT Filed: Nov. 4, 2009

(86) PCT No.: PCT/IE2009/000076
§ 371 (c)(1),
(2), (4) Date: Jun. 23, 2011

(87) PCT Pub. No.: WO2010/052692
PCT Pub. Date: May 14, 2010

(65) Prior Publication Data
US 2011/0264048 A1    Oct. 27, 2011

(30) Foreign Application Priority Data

| Nov. 4, 2008 | (IE) | S2008/0884 |
| Nov. 19, 2008 | (IE) | S2008/0925 |
| Dec. 19, 2008 | (IE) | S2008/1010 |
| May 27, 2009 | (IE) | S2009/0410 |
| Aug. 17, 2009 | (IE) | S2009/0629 |
| Aug. 17, 2009 | (IE) | S2009/0630 |

(51) Int. Cl.
A61M 5/00 (2006.01)
A61M 37/00 (2006.01)
(Continued)

(52) U.S. Cl.
CPC .......... *A61M 37/0015* (2013.01); *A61B 17/205* (2013.01); *A61B 2010/008* (2013.01);
(Continued)

(58) Field of Classification Search
CPC ............ A61M 5/3295; A61M 5/3298; A61M 25/0084; A61M 37/0015; A61M 2037/0023; A61M 2037/003; A61M 2037/0038; A61M 2037/0061; A61M 2037/0053; A61B 17/205; A61B 2010/008

USPC .......................... 604/46, 173, 890.1; 417/357
See application file for complete search history.

(56) References Cited

U.S. PATENT DOCUMENTS 4,340,048 A * 7/1982 Eckenhoff ................. 604/890.1
7,641,648 B2 * 1/2010 Bouphavichith et al. ..... 604/533
(Continued)

FOREIGN PATENT DOCUMENTS

WO    03/030984 A1    4/2003
WO    2006/060106 A1    6/2006
(Continued)

OTHER PUBLICATIONS

International Search Report for PCT/IE2009/000076 dated Mar. 3, 2010.

*Primary Examiner* — Theodore Stigell
(74) *Attorney, Agent, or Firm* — Sughrue Mion, PLLC

(57) ABSTRACT

A micro-needle delivery device (1) comprises an active substance accommodating layer (17) having active substance accommodating chambers (20) therein, a drive substance accommodating layer (32) having drive substance accommodating chambers (35) therein aligned with the active substance accommodating chambers (20), an activating layer (45) having heating elements (48) aligned with the drive substance accommodating chambers (35) for heating a drive substance therein, and a micro-needle element (8) having a needle support layer (9) and a plurality of micro-needles (12) extending therefrom. A burstable first membrane (22) is located between and sealably secured to the micro-needle element (8) and to the active substance accommodating layer (17) for sealably closing the active substance accommodating chambers (20) at one end. A second stretchable membrane (30) is located between and sealably secured to the drive substance accommodating layer (32) and to the active substance accommodating layer (17) sealably closes the active substance accommodating chambers (20) at the other end, and the drive substance accommodating chambers (35). A third membrane (40) sealably closes the drive substance accommodating chambers (35).

20 Claims, 10 Drawing Sheets

Figure 4:
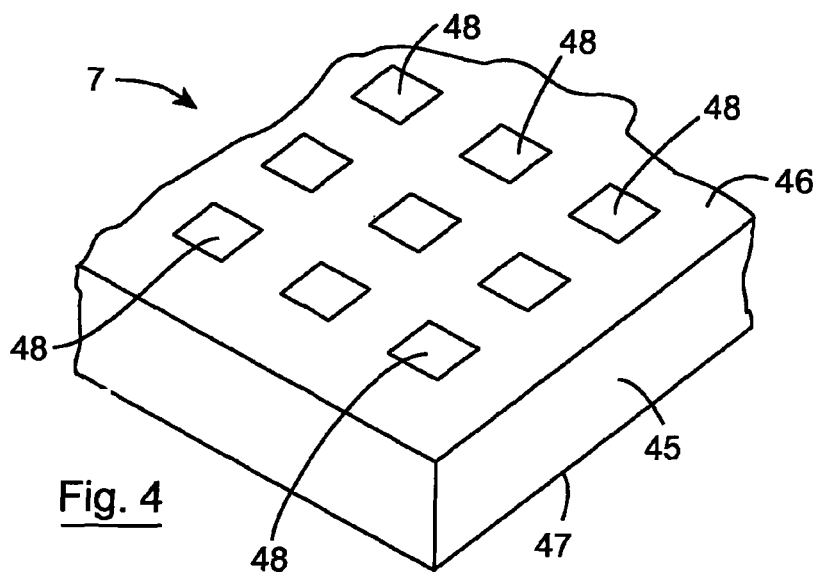

(51) Int. Cl.
 *A61B 17/20* (2006.01)
 *A61B 10/00* (2006.01)
(52) U.S. Cl.
 CPC .. *A61M2037/003* (2013.01); *A61M 2037/0023* (2013.01); *A61M 2037/0038* (2013.01); *A61M 2037/0053* (2013.01); *A61M 2037/0061* (2013.01)

(56) References Cited

U.S. PATENT DOCUMENTS

| | | |
|---|---|---|
| 2003/0083645 A1 | 5/2003 | Angel et al. |
| 2004/0115068 A1* | 6/2004 | Hansen et al. ............... 417/379 |
| 2006/0074376 A1 | 4/2006 | Kwon |
| 2006/0264926 A1 | 11/2006 | Kochamba |
| 2008/0015494 A1 | 1/2008 | Santini, Jr. et al. |

FOREIGN PATENT DOCUMENTS

| | | |
|---|---|---|
| WO | 2008/008557 A1 | 1/2008 |
| WO | 2008/101892 A1 | 8/2008 |
| WO | 2009/069112 A1 | 6/2009 |

* cited by examiner

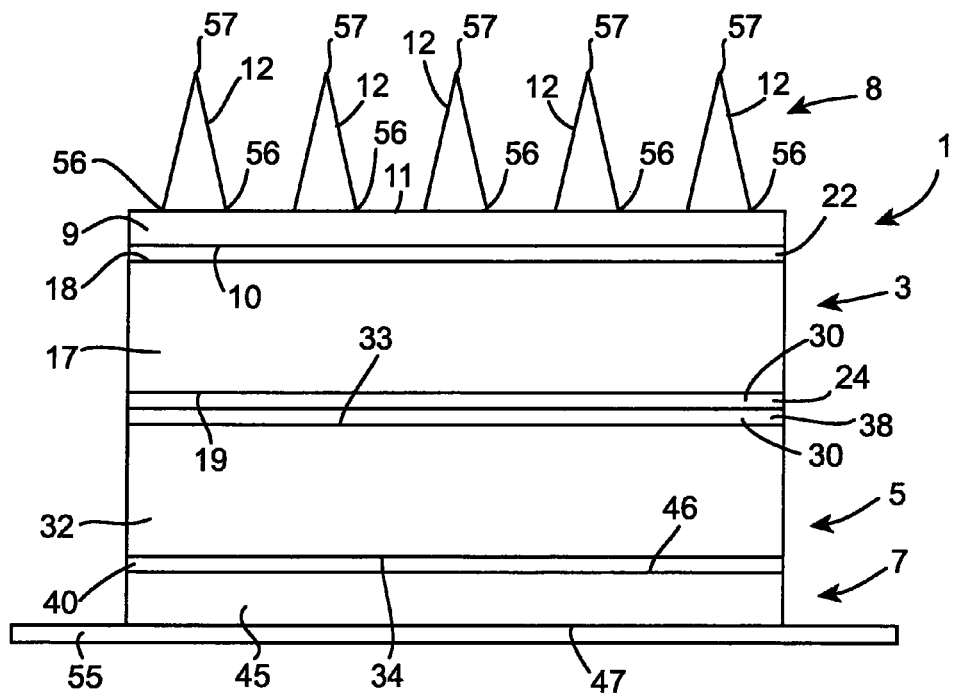
Fig. 1
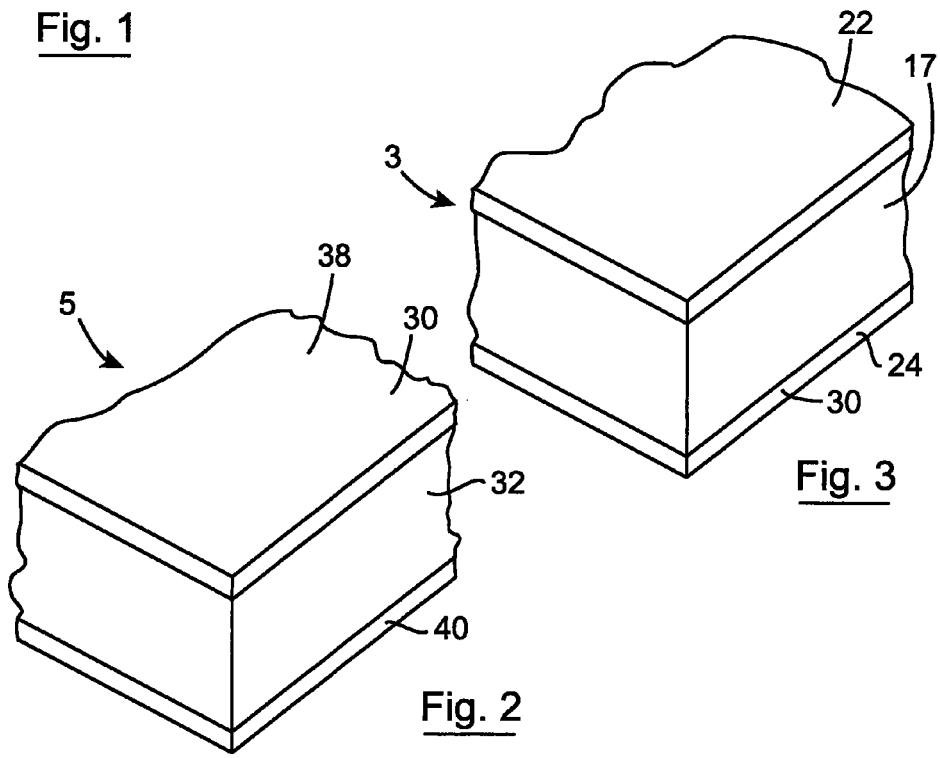
Fig. 2
Fig. 3

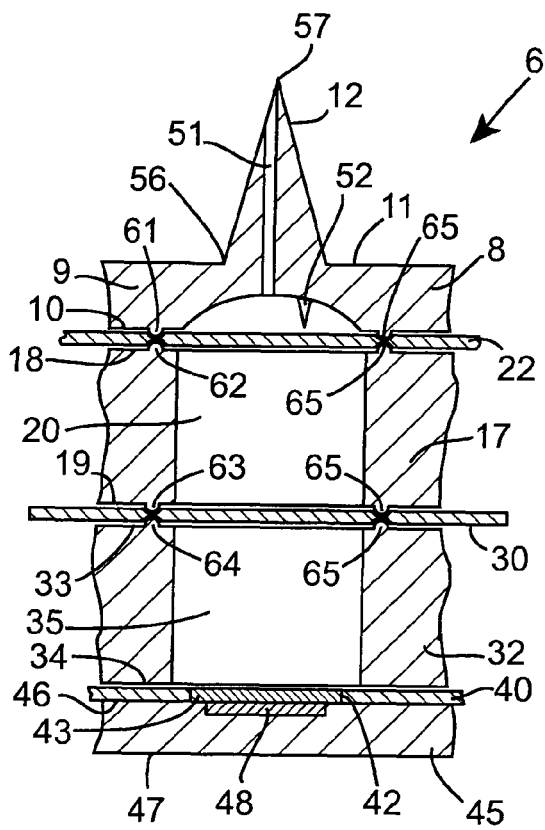
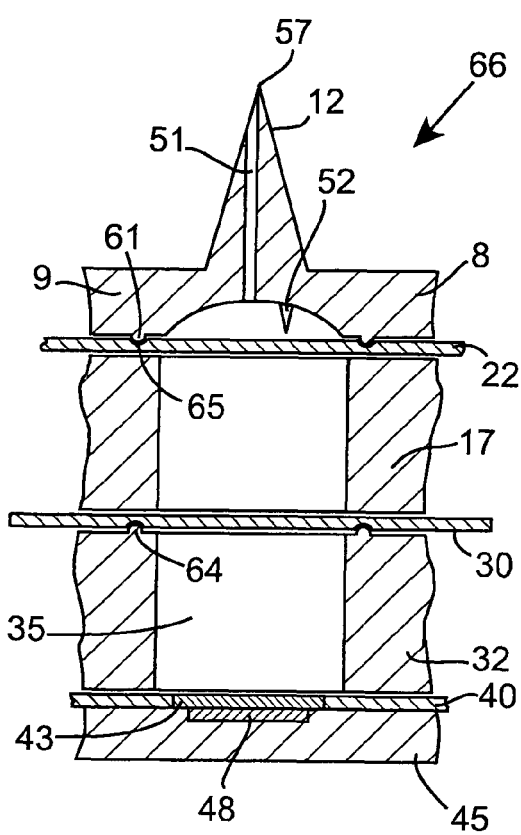
Fig. 7
Fig. 9
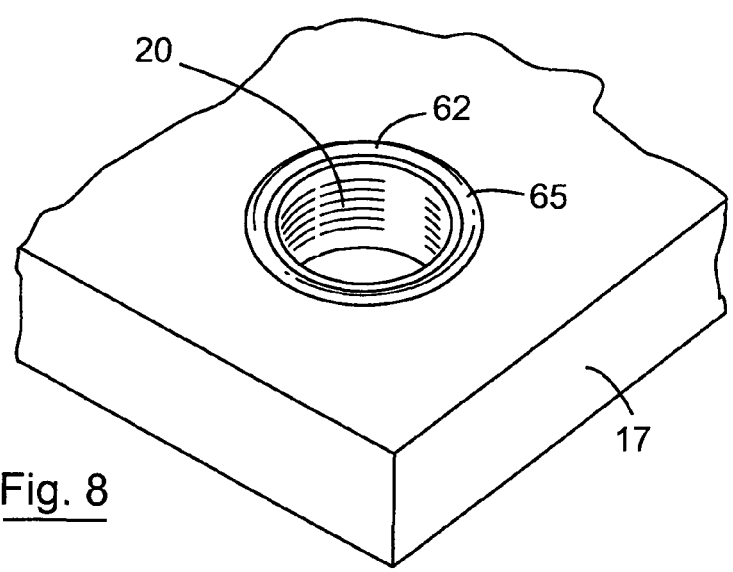
Fig. 8

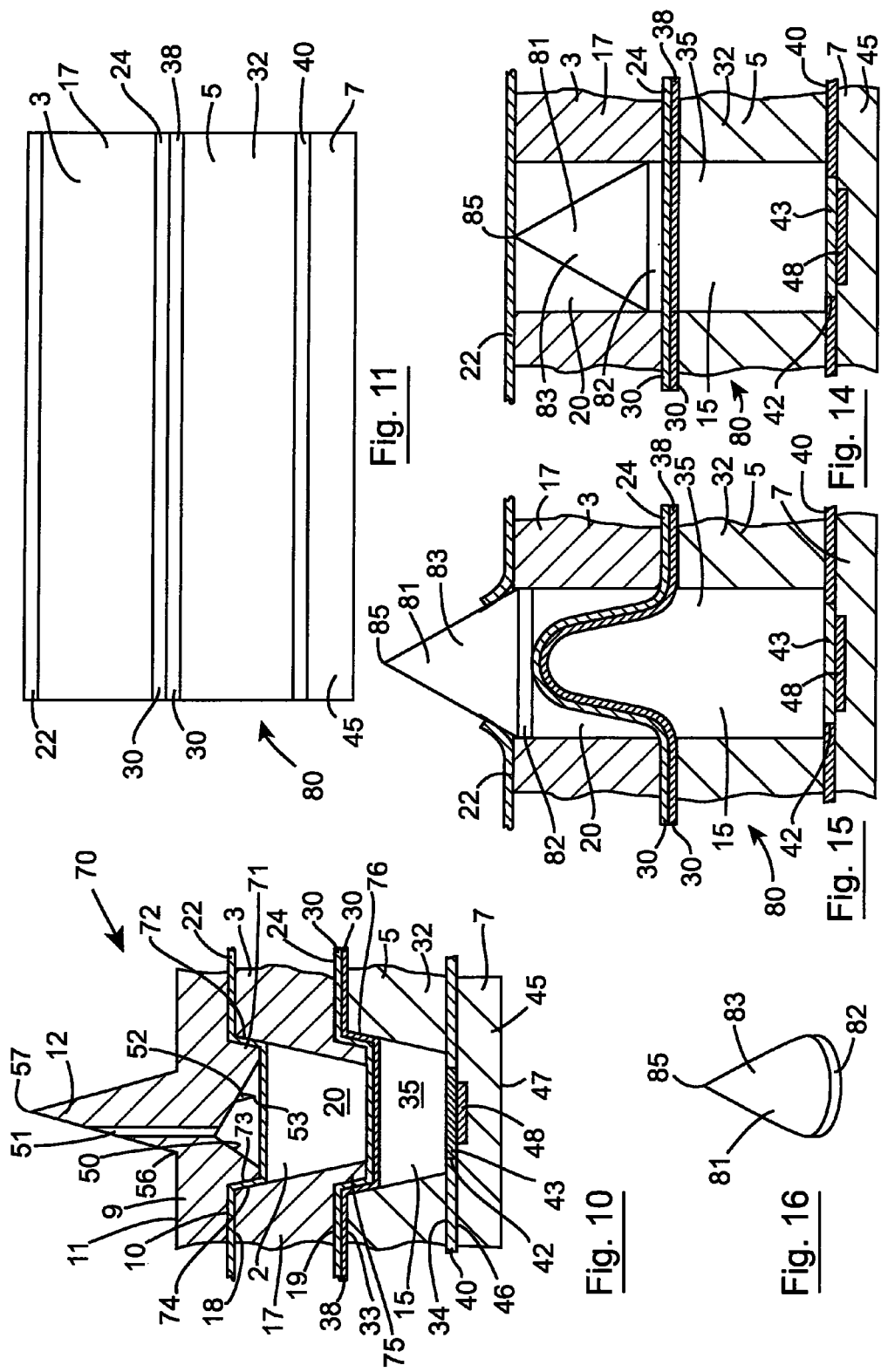

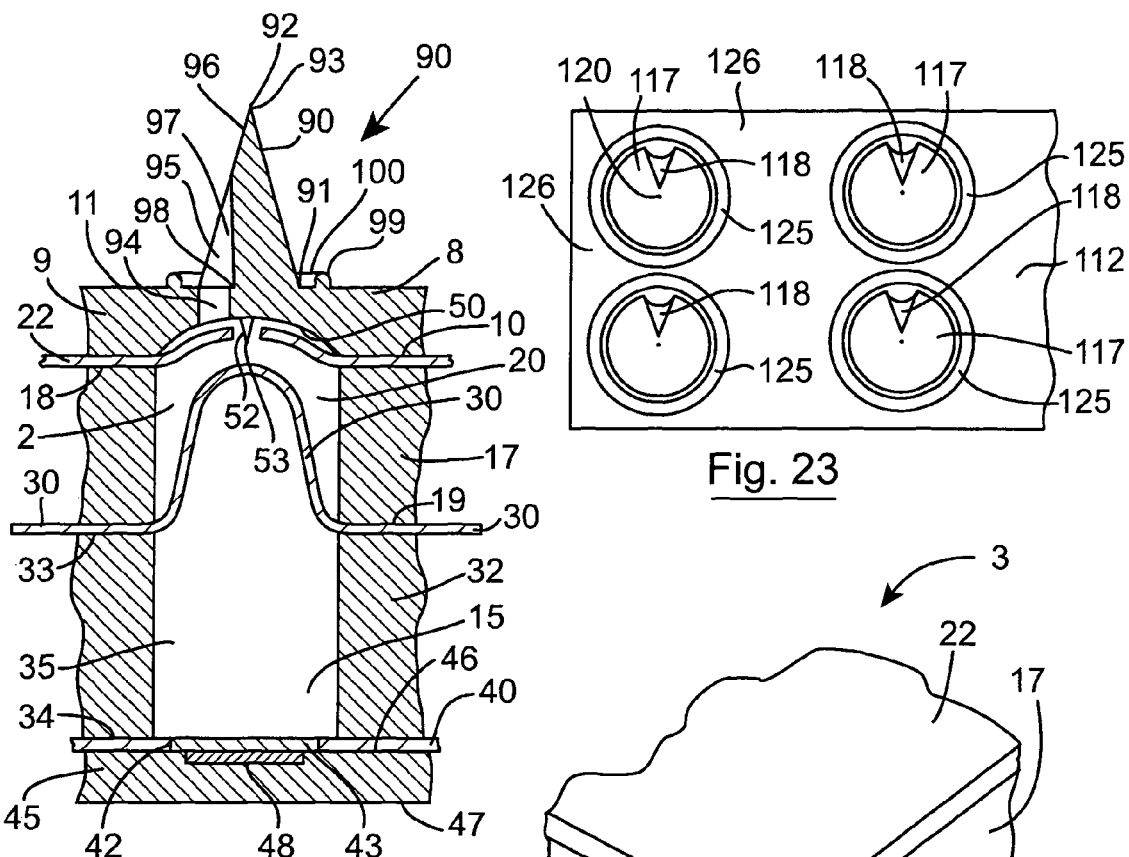
Fig. 23
Fig. 19
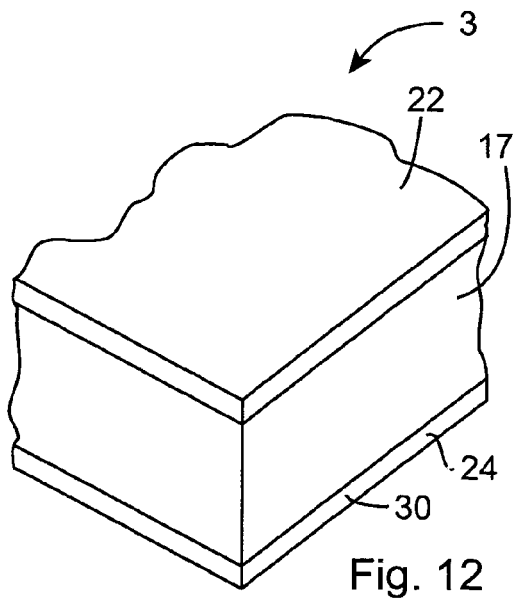
Fig. 12
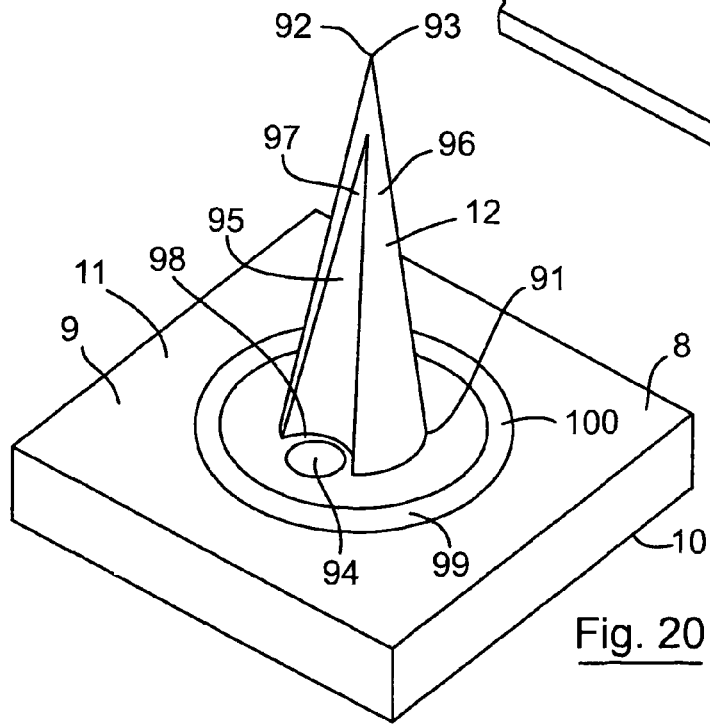
Fig. 20

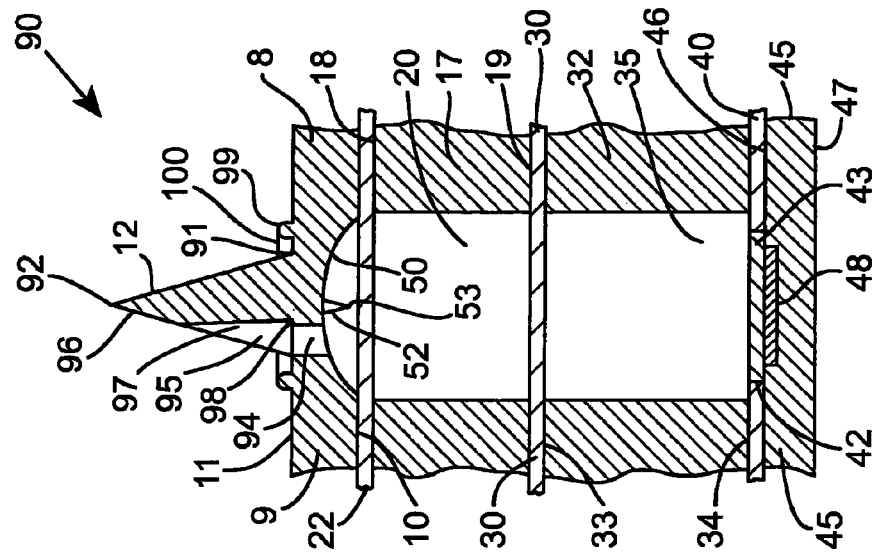
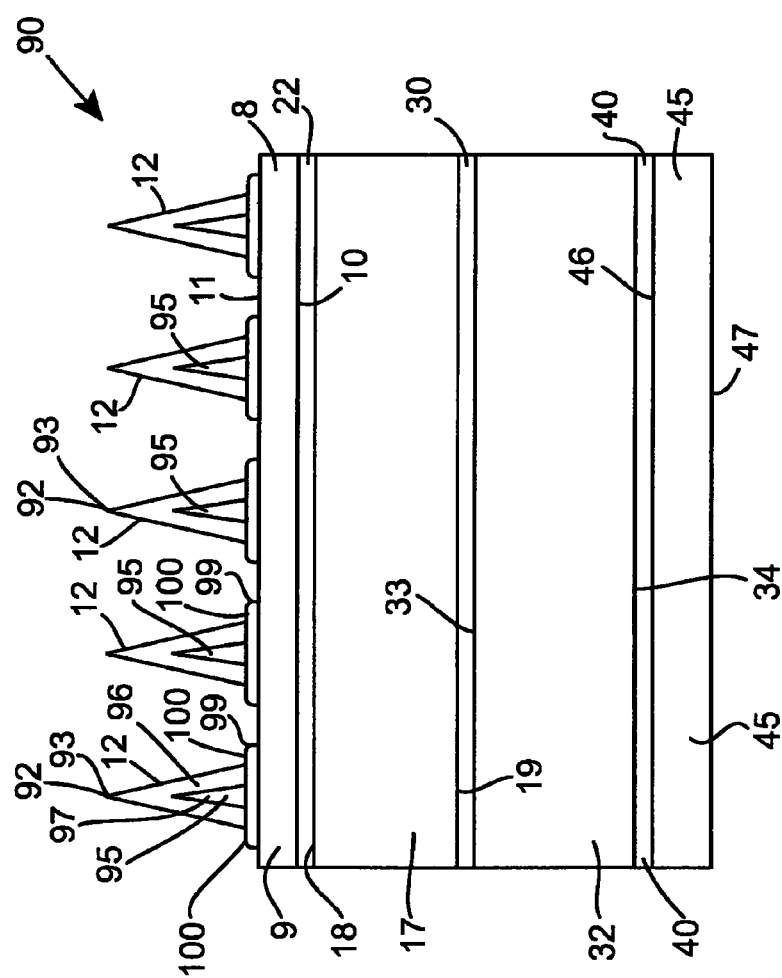
Fig. 18
Fig. 17

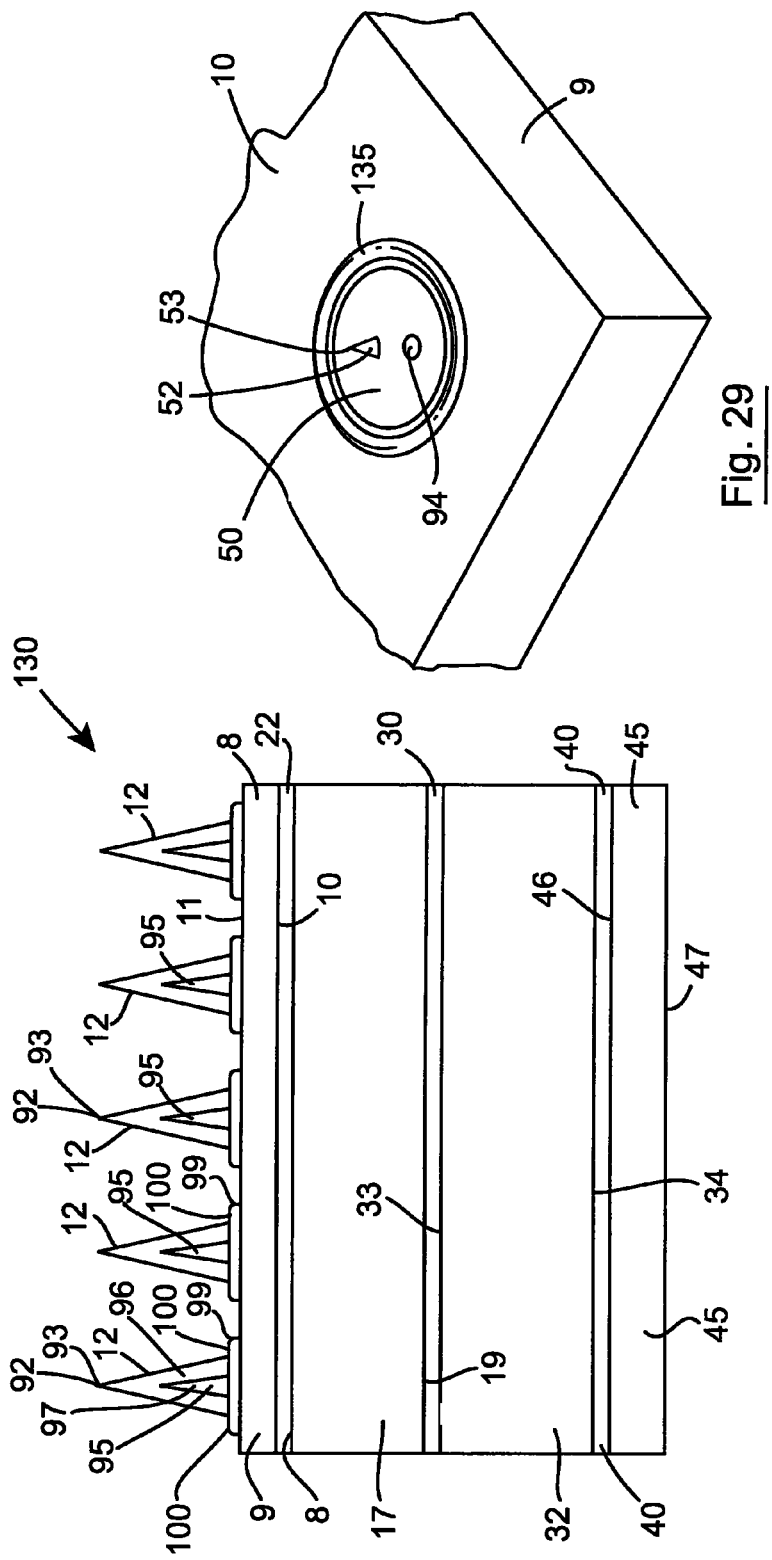

TRANSFER DEVICE FOR TRANSFERRING A SUBSTANCE BETWEEN THE DEVICE AND A SUBJECT

The present invention relates to a transfer device for transferring a substance between the device and a subject, for example, a delivery device for delivering an active substance transdermally or subcutaneously from the device to the subject, or a transfer device for withdrawing a sample of a bodily substance, for example, a bodily fluid from a subject into the device. The invention also relates to a kit of parts for assembly to form a transfer device or a delivery device according to the invention, and the invention relates to an active substance cartridge for containing an active substance, a drive substance cartridge for containing a drive substance, a micro-needle element comprising a micro-needle support layer having a plurality of micro-needles extending therefrom. The invention also relates to a method for providing a transfer device or a delivery device according to the invention from the cartridges according to the invention, and the invention relates to a method for moulding a micro-needle element.

Such transfer devices are known. In general, such micro-transfer devices comprise an active substance accommodating layer which comprises a plurality of active substance chambers within which the active substance is stored for delivery to the subject, or into which the sample of bodily fluid is withdrawn from the subject. The active substance chambers are arranged in a matrix. A drive substance accommodating layer is provided with a plurality of drive substance accommodating chambers arranged in a matrix corresponding to the matrix of the active substance accommodating chambers for accommodating a drive substance. The drive substance accommodating chambers are aligned with the active substance accommodating chambers. A stretchable membrane is located between the active substance accommodating layer and the drive substance accommodating layer, so that as the drive substance expands in each drive substance accommodating chamber, the stretchable membrane is urged into the corresponding active substance accommodating chamber for urging the active substances from the active substance accommodating chamber.

A micro-needle support layer having a plurality of micro-needles arranged in a matrix corresponding to the matrix in which the active substance accommodating chambers are arranged is provided adjacent the active substance accommodating layer with the micro-needles aligned with the active substance accommodating chambers. A burstable membrane is located between the active substance accommodating layer and the micro-needle support layer. Each micro-needle is provided with a bore extending therethrough and in turn through the micro-needle support layer to communicate with the corresponding active substance accommodating chamber.

The burstable membrane and the stretchable membrane seal the active substance into the active substance accommodating chambers at respective opposite ends thereof. However, when pressure is applied by the drive substance to the stretchable membrane, the stretchable membrane in turn stretches and is urged into the corresponding active substance accommodating chamber, thereby applying pressure to the active substance therein. The pressure generated in the active substance results in bursting of the burstable membrane, which thereby permits communication between the active substance accommodating chamber and the corresponding micro-needle for delivering the active substance from the active substance accommodating chamber through the micro-needle to the subject.

An activating layer which comprises a plurality of independently addressable heating elements which are arranged in a matrix corresponding to the matrix of the drive substance accommodating chambers is secured to the drive substance accommodating layer with the heating elements aligned with the drive substance accommodating chambers. A membrane is located between the activating layer and the drive substance accommodating layer. The membrane seals one end of the drive substance accommodating chambers, while the other end thereof is sealed by the stretchable membrane located between the active substance accommodating layer and the drive substance accommodating layer for sealably retaining the drive substance within the drive substance accommodating chambers. Heating of the heating elements on the activating layer heats the drive substance in the corresponding drive substance accommodating chambers, which expands to urge the stretchable membrane into the corresponding active substance accommodating chamber or chambers.

Where the transfer device is provided for withdrawing a sample of bodily fluid from a subject for storing in one or more of the active substance accommodating chambers, the drive substance in the corresponding drive substance accommodating chambers would be of the type which contracts. The stretchable membrane would initially be located in the active substance accommodating chamber, and on contraction of the drive substance the stretchable membrane would be withdrawn from the active substance accommodating chamber in order to draw a vacuum in the active substance accommodating chamber to in turn draw the fluid sample from the subject into the corresponding one or more of the active substance accommodating chambers.

Such transfer devices suffer from a number of disadvantages. Firstly, in all cases they may not be suitable for active substances or bodily samples of relatively large molecule size, secondly, production of such micro-transfer devices is complex and complicated, and in many cases, it is difficult to achieve adequate sealing between the respective layers and the membranes therebetween.

There is therefore a need for a transfer device which addresses at least one of these problems of known transfer and delivery devices.

The present invention is directed towards providing such a transfer device, and the invention is also directed towards a method for providing a transfer device which addresses one or more of the problems of known transfer devices. The invention is also directed towards providing a micro-needle element and a method for moulding the micro-needle element. The invention is also directed towards a micro-delivery device, and to an active substance cartridge, and to a drive substance cartridge, which are suitable for assembling to form a transfer or a delivery device.

According to the invention there is provided a transfer device for transferring a substance between the device and a subject, the device comprising a first layer having a pair of opposite major surfaces and at least one storage chamber extending into the first layer from at least one of the major surfaces thereof, a second layer having a first major surface, the second layer being one of a drive substance accommodating layer having at least one drive substance accommodating chamber therein, and a needle support layer having at least one micro-needle extending therefrom, the second layer having at least one communicating means communicating the corresponding one of the at least one drive substance accommodating chamber and the at least one micro-needle through the first major surface thereof, a membrane located between the first major surface of the second layer and the major surface of the first layer from which the at least one storage chamber extends therein, and a means for effecting a seal between the membrane and at least one of the adjacent major surfaces of one of the first layer and the second layer adjacent the corresponding one of the at least one storage chamber and the at least one communicating means.

Preferably, the means for effecting a seal between the membrane and the at least one of the adjacent major surface of one of the first layer and the second layer effects a seal to extend completely around the corresponding one of the at least one storage chamber and the at least one communicating means.

In one embodiment of the invention the means for effecting a seal between the membrane and the at least one of the adjacent major surface of one of the first layer and the second layer is adapted for effecting a seal between the membrane and the adjacent major surface of the first layer and comprises a seal effecting projecting element extending from one of the adjacent major surfaces of the one of the first layer and the second layer for engaging the membrane. Preferably, the seal effecting projecting element terminates in a membrane abutting surface. Ideally, the membrane abutting surface of the seal effecting projecting element is radiused.

In one embodiment of the invention the seal effecting projecting element is of annular configuration extending around the corresponding one of the at least one storage chamber and the at least one communicating means, and preferably, the seal effecting projecting element is of ridge shape configuration, and the seal effecting projecting element extends from the major surface of the first layer.

Advantageously, the seal effecting projecting element extends from the first major surface of the second layer.

In another embodiment of the invention the means for effecting a seal between the membrane and the adjacent major surface of the first layer comprises respective ones of the seal effecting projecting elements extending from both of the major surfaces of the first layer and the second layer adjacent the membrane.

In a further embodiment of the invention the means for effecting a seal between the membrane and at least one of the adjacent major surfaces of one of the first layer and the second layer comprises a pair of interengageable complementary seal effecting formations for engaging the membrane therebetween, one of the pair of seal effecting formations being formed on one of the adjacent major surfaces of one of the first layer and the second layer, and the other of the seal effecting formations being formed on the other of the adjacent major surfaces of the first layer and the second layer.

In one embodiment of the invention one of the seal effecting formations comprises a seal effecting recess formed into the adjacent major surface of one of the first layer and the second layer. Preferably, the seal effecting recess is of annular configuration. Advantageously, the seal effecting recess extends around the corresponding one of the at least one storage chamber and the at least one communicating means. Preferably, the seal effecting recess extends into the at least one storage chamber and the at least one communicating means adjacent the corresponding major surface thereof. Advantageously, the seal effecting recess tapers inwardly from the corresponding major surface.

Advantageously, the other of the seal effecting formations comprises one of the seal effecting projecting elements for engaging the corresponding seal effecting recess with the membrane engaged therebetween. Preferably, the seal effecting projecting element tapers inwardly from the corresponding major surface of the corresponding one of the first layer and second layer. Advantageously, the seal effecting projecting element tapers inwardly from the corresponding major surface of the corresponding one of the first layer and the second layer at an angle corresponding to the angle at which the corresponding seal effecting recess tapers inwardly from the corresponding major surface of the corresponding one of the first layer and the second layer.

In a further embodiment of the invention the means for effecting a seal between the membrane and the at least one of the adjacent major surfaces of one of the first layer and the second layer comprises a gasket located between the membrane and the adjacent major surface with which a seal is to be effected, the gasket having at least one opening therethrough for communicating with a corresponding one of the at least one storage chamber in the first layer and the at least one communicating means in the second layer. Preferably, the gasket is recessed into the adjacent major surface with which a seal is to be effected.

In one embodiment of the invention a corresponding one of the seal effecting projecting elements extending from the other of the major surfaces adjacent the membrane which engages the membrane urges the gasket into engagement with the major surface of the one of the first layer and the second layer against which the gasket is adjacent through the membrane.

In one embodiment of the invention the second layer is the needle support layer, and the membrane located between the first layer and the needle support layer is a first membrane of a burstable material to provide communication between the at least one storage chamber in the first layer and a corresponding one of the at least one communicating means of the needle support layer for accommodating a substance between the at least one storage chamber and a corresponding one of the at least one micro-needle of the needle support layer.

In another embodiment of the invention the first membrane is burstable adjacent the at least one storage chamber in response to one of a positive pressure and a negative pressure being applied thereto from the storage chamber. Preferably, the first membrane is burstable adjacent the at least one storage chamber in response to a positive pressure being applied thereto from the storage chamber.

In another embodiment of the invention the needle support layer defines a second major surface opposite the first major surface, and the at least one micro-needle extends from the second major surface of the needle support layer.

In another embodiment of the invention the at least one communicating means of the needle support layer for communicating with the at least one micro-needle comprises a first communicating means extending through the needle support layer and a second communicating means extending along an outer surface of the at least one micro-needle communicating with the first communicating means for accommodating a substance along the micro-needle.

Preferably, the first communicating means comprises a communicating bore extending through the needle support layer. Advantageously, the communicating bore extends into the needle support layer adjacent the needle. Preferably, the communicating bore extends into the needle support layer adjacent the second communicating means.

In one embodiment of the invention the second communicating means extends along the outer surface of the micro-needle, so that the micro-needle forms a seal with the skin of the subject adjacent the second communicating means for accommodating the transdermally. Preferably, the second communicating means is defined by an elongated communicating channel formed in or on the outer surface of the micro-needle. Advantageously, the communicating channel extends along the micro-needle from a proximal end thereof and communicates with the first communicating means adjacent the proximal end of the micro-needle. Advantageously, the communicating channel terminates adjacent but spaced apart from a distal end of the micro-needle. Ideally, the communicating channel extends in a generally axial direction towards the distal end of the micro-needle. Preferably, the communicating channel tapers in a direction towards the distal end of the micro-needle. Ideally, the communicating channel is formed by a communicating recess which is formed into the outer surface of the micro-needle.

In another embodiment of the invention the communicating bore extends into the needle support layer adjacent the proximal end of the micro-needle in an area of the needle support layer defined by the communicating channel.

In a further embodiment of the invention a sealing means is provided for forming a seal between the second major surface of the needle support layer and the skin of the subject to minimise loss of a substance as the substance is passing between the first and second communicating means. Preferably, the sealing means extends from the needle support layer adjacent the first communicating means. Advantageously, the sealing means is configured as an annular sealing means. Ideally, the sealing means extends around the at least one micro-needle with the first communicating means contained within the sealing means.

In one embodiment of the invention the sealing means comprises a ridge type sealing element extending from the second major surface of the needle support layer and adapted for sealable engagement with the skin of a subject. Preferably, the ridge type sealing element terminates in a radiused skin abutting surface which is convex when viewed in plan.

In another embodiment of the invention the sealing means comprises an O-ring seal located in a groove formed in the second major surface in the needle support layer. Preferably, the groove for accommodating the O-ring seal extends around the micro-needle for accommodating the O-ring seal around the needle.

In one embodiment of the invention the at least one micro-needle terminates at the distal end thereof in a pointed tip. Preferably, the at least one micro-needle tapers from the proximal end to the distal end to define the pointed tip. Advantageously, the at least one micro-needle is of circular transverse cross-section.

In one embodiment of the invention the second communicating means comprises a second communicating bore extending through the micro-needle. Preferably, the second communicating bore is located in the micro-needle offset from a central axis thereof. Advantageously, the first communicating means comprises a communicating cavity formed into the needle support layer from the first major surface thereof, and the second communicating bore extends through the micro-needle from the communicating cavity. Advantageously, the second communicating bore is offset from the central axis of the micro-needle.

In one embodiment of the invention a plurality of micro-needles are provided extending from the needle support layer. Preferably, the micro-needles are configured in an array.

In one embodiment of the invention each storage chamber extends between the opposite major surfaces of the first layer.

Preferably, a plurality of storage chambers are provided in the first layer. Advantageously, the storage chambers in the first layer are configured in a matrix.

In one embodiment of the invention the first membrane is selectively burstable adjacent the respective active substance accommodating chambers. Preferably, the first membrane is impermeable to a substance in the at least one storage chamber.

Advantageously, the at least one micro-needle in the needle support layer is aligned with a corresponding one of the at least one storage chambers in the first layer.

In one embodiment of the invention the second layer is the drive substance accommodating layer, and the membrane located between the first layer and the drive substance accommodating layer is a second membrane of a stretchable material. Advantageously, the communicating means to the at least one drive substance accommodating chamber is defined by a corresponding open mouth to the drive substance accommodating chamber formed in the first major surface of the drive substance accommodating layer.

In one embodiment of the invention the second membrane is adapted to stretch into the at least one storage chamber in the first layer corresponding to the at least one drive substance chamber in the drive substance layer. In another embodiment of the invention an activating means is provided for co-operating with a drive substance in the at least one of the drive substance accommodating chambers for one of urging the second membrane into the corresponding at least one storage chamber and urging the second membrane out of the corresponding at least one storage chamber. Preferably, the activating means is adapted for co-operating with the drive substance in the at least one of the drive substance accommodating chambers for urging the second membrane into the corresponding at least one storage chamber for urging a substance in the storage chamber from the storage chamber. Advantageously, the activating means is adapted for co-operating with the drive substance in the at least one of the drive substance accommodating chambers for urging the second membrane out of the corresponding at least one storage chamber for drawing a substance into the storage chamber.

In one embodiment of the invention the drive substance accommodating layer defines a second major surface opposite the first major surface thereof, and the activating means is located adjacent the second major surface of the drive substance accommodating layer. Preferably, the activating means is located on an activation layer provided to abut the second major surface of the drive substance accommodating layer with the activating means adjacent the at least one drive substance accommodating chambers. Advantageously, each activating means comprises a heating element.

In another embodiment of the invention the at least one drive substance accommodating chamber extends between the first and second major surfaces of the drive substance accommodating layer, and a third membrane is located adjacent the second major surface of the drive substance accommodating layer for sealably closing the at least one drive substance accommodating chamber adjacent the second major surface of the drive substance accommodating layer.

In another embodiment of the invention the third membrane is impermeable to the drive substance.

In another embodiment of the invention a plurality of drive substance accommodating chambers are provided. Preferably, the drive substance accommodating chambers are configured in a matrix. Advantageously, the at least one storage chamber in the first layer is aligned with a corresponding one of the drive substance chambers. Ideally, the second membrane is impermeable to the drive substance in the at least one drive substance accommodating chamber. Preferably, the second membrane is of a material impermeable to a substance located in the at least one chamber in the first layer.

In one embodiment of the invention the substance to be one of urged into and urged out of the at least one storage chamber in the first layer is in a liquid form.

In another embodiment of the invention the substance to be urged out of the at least one storage chamber of the first layer is in a solid form.

In one embodiment of the invention the substance in the solid form is contained in a solid form structure. In another embodiment of the invention the solid form structure terminates in a pointed tip and is adapted to be urged from the at least one storage chamber through the membrane attached to the major surface of the first layer opposite to the major surface of the first layer adjacent which the second layer is located to penetrate the skin of a subject with the pointed tip. Alternatively, the solid form structure is of one of a spherical shape, a parallelepiped shape or other three-dimensional shape, which preferably is provided with a roughened surface, and is adapted to be urged from the at least one storage chamber through the membrane attached to the major surface of the first layer opposite to the major surface of the first layer adjacent which the second layer is located to penetrate the skin of the subject.

In another embodiment of the invention the transfer device is adapted for transferring an active substance in the at least one storage chamber in the first layer transdermally to a subject.

In a further embodiment of the invention the transfer device is adapted for withdrawing a substance from a subject transdermally to the at least one storage chamber in the first layer.

Preferably, a securing means is provided for securing the transfer device to the skin of a subject.

The invention also provides an active substance cartridge for use in the transfer device according to the invention wherein the active substance cartridge comprises the first layer, an active substance contained in at least some of the storage chambers in the first layer, and the first and second membranes sealably secured to the respective opposite major surfaces of the first layer with the respective active substances sealably contained within the storage chambers.

The invention also provides a drive substance cartridge for use in the transfer device according to the invention wherein a drive substance is provided in at least some of the drive substance accommodating chambers of the second layer, and the second membrane is sealably secured to the first major surface of the second layer for sealably closing the drive substance accommodating chambers adjacent the first major surface of the second layer.

Preferably, each drive substance accommodating chamber extends between the first and second major surfaces of the second layer, and a third membrane is sealably secured to the second major surface of the second layer for sealably closing the drive substance accommodating chambers adjacent the second major surface of the second layer.

The invention also provides a micro-needle element for a micro-needle fluid transfer device, the micro-needle element comprising a needle support layer adapted for attaching to a storage cartridge, and having at least one micro-needle extending from the micro-needle support layer, a first communicating means extending through the needle support layer for communicating with the storage cartridge, and a second communicating means extending along an outer surface of the at least one micro-needle communicating with the first communicating means for accommodating a fluid between the needle and the storage cartridge when attached thereto.

Preferably, the first communicating means comprises a communicating bore extending through the needle support layer. Advantageously, the communicating bore extends into the needle support layer adjacent the micro-needle. Preferably, the communicating bore extends into the needle support layer adjacent the second communicating means.

In one embodiment of the invention the second communicating means extends along the outer surface of the micro-needle, so that the micro-needle forms a seal with the skin of the subject adjacent the second communicating means for accommodating a fluid transdermally. Preferably, the second communicating means is defined by an elongated communicating channel formed in or on the outer surface of the micro-needle. Advantageously, the communicating channel extends along the micro-needle from a proximal end thereof and communicates with the first communicating means adjacent the proximal end of the micro-needle. Preferably, the communicating channel terminates adjacent but spaced apart from a distal end of the micro-needle. Advantageously, the communicating channel extends in a generally axial direction towards the distal end of the micro-needle. Preferably, the communicating channel tapers in a direction towards the distal end of the micro-needle. Ideally, the communicating channel is formed by a communicating recess which is formed into the outer surface of the micro-needle.

In one embodiment of the invention the communicating bore extends into the needle support layer adjacent the proximal end of the micro-needle in an area of the needle support layer defined by the communicating channel.

In another embodiment of the invention a sealing means is provided for forming a seal between the needle support layer and the skin of the subject to minimise fluid loss as the fluid is passing between the first and second communicating means.

The invention further provides an active substance cartridge for use in a delivery device for delivering an active substance to a subject, the active substance cartridge comprising an active substance accommodating layer defining first and second opposite major surfaces and defining a plurality of discrete active substance accommodating chambers extending through the active substance accommodating layer between the first and second major surfaces, the active substance being located in at least some of the active substance accommodating chambers, a first membrane abutting and sealably secured to the first major surface of the active substance accommodating layer sealably closing the active substance accommodating chambers adjacent the first major surface thereof, a second membrane abutting and sealably secured to the second major surface of the active substance accommodating layer sealably closing the active substance accommodating chambers adjacent the second major surface of the active substance accommodating layer, the cartridge being adapted for co-operating with a drive means for urging the active substance from the active substance accommodating chambers for delivery to the subject.

In one embodiment of the invention the active substance cartridge is adapted to co-operate with the drive means so that the active substance cartridge is located with the second membrane adjacent the drive means. Preferably, the second membrane is urgeable into the respective active substance accommodating chambers for urging the active substance therefrom. Advantageously, the second membrane is of a stretchable material.

In one embodiment of the invention the first membrane is rupturable adjacent the respective active substance accommodating chambers in response to the second membrane being urged into the corresponding active substance accommodating chamber.

In one embodiment of the invention the first membrane is of a foil material.

In another embodiment of the invention the first membrane is of a metal foil material. Alternatively, the first membrane is of a plastics material.

In one embodiment of the invention the active substance is provided in liquid form.

In another embodiment of the invention the active substance cartridge is adapted to co-operate with a skin penetrating means for delivery of the active substance to the subject. Advantageously, the skin penetrating means comprises a micro-needle element, the micro-needle element comprising a needle support layer and a plurality of micro-needles extending from the needle support layer.

Preferably, the active substance accommodating chambers are adapted to co-operate with respective corresponding ones of the micro-needles for delivering the active substance to the subject. Advantageously, rupturing of the first membrane adjacent the respective active substance accommodating chambers facilitates communication between the active substance accommodating chambers and the respective corresponding micro-needles.

In another embodiment of the invention the active substance is provided in a solid form structure.

In one embodiment of the invention one of the solid form structures comprising the active substance is provided in each active substance accommodating chamber.

Preferably, a means for effecting a seal between the first major surface of the active substance accommodating layer and the first membrane adjacent each active substance accommodating chamber is provided.

In one embodiment of the invention the means for effecting a seal between the first major surface of the active substance accommodating layer and the first membrane comprises a gasket located therebetween, the gasket having a plurality of active substance accommodating openings at locations corresponding to the respective active substance chambers.

In another embodiment of the invention the means for effecting a seal between the first major surface of the active substance accommodating layer and the first membrane adjacent each active substance accommodating chamber comprises one of a pair of interengageable complementary seal effecting formations, the said one of the interengageable complementary seal effecting formations being formed on the first major surface of the active substance accommodating layer for engaging the corresponding one of the interengageable complementary seal effecting formations located on the needle support layer of the micro-needle element with which the active substance cartridge is to co-operate.

Preferably, the said one of the seal effecting formations comprises one of a seal effecting projecting element extending from the first major surface of the active substance accommodating layer adjacent the active substance accommodating chamber, and a seal effecting recess formed into the first major surface of the active substance accommodating layer adjacent the active substance accommodating chamber.

Advantageously, each of the ones of the seal effecting projecting elements and the seal effecting recesses is of annular configuration extending around the corresponding one of the active substance accommodating chamber.

Advantageously, each of the said seal effecting formations comprises one of the seal effecting recesses. Preferably, each seal effecting recess extends into the active substance accommodating chamber adjacent the first major surface of the active substance accommodating layer.

Preferably, the active substance accommodating chambers are configured in the active substance accommodating layer in the form of a matrix.

The invention also provides a drive cartridge for use in a delivery device for delivering an active substance to a subject, the drive cartridge comprising a drive substance accommodating layer defining opposite first and second major surfaces and defining a plurality of discrete drive substance accommodating chambers extending into the drive substance accommodating layer from the first major surface thereof, a drive substance being provided in at least some of the drive substance accommodating chambers, a second membrane abutting and sealably secured to the first major surface of the drive substance accommodating layer sealably closing the drive substance accommodating chambers adjacent the first major surface of the drive substance accommodating layer, the drive substance cartridge being adapted to co-operate with an active substance cartridge for urging an active substance from active substance accommodating chambers for delivery to a subject.

Preferably, the drive substance is an expandable substance. Advantageously, the drive substance is expandable in response to temperature change.

Ideally, the second membrane is of a stretchable material for accommodating expansion of the drive substance.

In another embodiment of the invention the second membrane of the drive cartridge is co-operable with a second membrane of the active substance cartridge with which the drive cartridge is adapted to co-operate for urging the second membrane of the active substance cartridge into respective active substance accommodating chambers thereof for in turn urging the active substance in the respective active substance accommodating chambers therefrom.

In another embodiment of the invention an activating means is provided co-operable with the drive substance in the respective drive substance accommodating chambers of the drive substance accommodating layer for causing the drive substance to expand. Preferably, the activating means is adapted for altering the temperature of the drive substance.

In another embodiment of the invention each drive substance accommodating chamber terminates in the drive substance accommodating layer short of the second major surface thereof to form a well extending into the drive substance accommodating layer from the first major surface thereof. Preferably, each drive substance accommodating chamber extends from the first major surface to the second major surface of the drive substance accommodating layer.

Advantageously, a third membrane is provided abutting and sealably secured to the second major surface of the drive substance accommodating layer sealably closing the drive substance accommodating chambers adjacent the second major surface of the drive substance accommodating layer.

Preferably, the activating means is provided separately of the drive cartridge, and is adapted for securing to the drive cartridge. Advantageously, the activating means is adapted for securing to the drive cartridge adjacent the third membrane thereof.

In another embodiment of the invention an activation cartridge is provided for accommodating the activating means, the activation cartridge being adapted to be secured to the third membrane. Preferably, a plurality of activating means are provided on the activation cartridge corresponding to respective ones of the drive substance accommodating chambers. Advantageously, the activating means are aligned with respective corresponding ones of the drive substance accommodating chambers. Preferably, the drive substance accommodating chambers are configured in the drive substance accommodating layer in a matrix. In one embodiment of the invention a means for effecting a seal between the first major surface of the drive substance accommodating layer and the second membrane is provided adjacent each drive substance accommodating chamber.

In another embodiment of the invention the means for effecting a seal between the first major surface of the drive substance accommodating layer and the second membrane adjacent each drive substance accommodating chamber comprises one of a pair of interengageable complementary seal effecting formations, the said one of the interengageable complementary seal effecting formations being formed on the first major surface of the drive substance accommodating layer for engaging the corresponding one of the interengageable complementary seal effecting formations located on an adjacent active substance accommodating layer of the drive substance cartridge with which the drive substance cartridge is to co-operate.

Preferably, the said one of the seal effecting formations comprises one of a seal effecting projecting element extending from the first major surface of the drive substance accommodating layer adjacent the drive substance accommodating chamber and a seal effecting recess formed into the first major surface of the drive substance accommodating layer adjacent the drive substance accommodating chamber. Advantageously, each of the ones of the seal effecting projecting elements and the seal effecting projecting recesses is of annular configuration extending around the corresponding one of the drive substance accommodating chamber. Advantageously, each of the said seal effecting formations comprises one of the seal effecting recesses. Ideally, each seal effecting recess extends into the drive substance accommodating chamber adjacent the first major surface of the drive substance accommodating layer.

The invention also provides a delivery device in kit form for delivering an active substance to a subject, the delivery device comprising an active substance cartridge according to the invention and a drive substance cartridge according to the invention, the drive substance cartridge being adapted to be secured to the active substance cartridge with the second membranes of the respective active and drive substance cartridges abutting each other, and with at least some of the drive substance cartridges aligned with at least some of the active substance cartridges.

Preferably, the respective means for effecting a seal between the respective second membranes and the corresponding adjacent major surfaces of the active and drive substance cartridges are co-operable with each other for effecting the respective seals.

In another embodiment of the invention the delivery device further comprises a micro-needle element, the micro-needle element comprising a needle support layer having a plurality of micro-needles extending therefrom, the needle support layer being adapted for securing to the first membrane of the active substance cartridge, with at least some of the micro-needles aligned with corresponding ones of the active substance accommodating chambers.

Advantageously, a seal effecting means is provided for effecting a seal between the first membrane and the active substance accommodating layer adjacent the active substance accommodating chambers, each seal effecting means comprising one of a seal effecting projecting element extending from the micro-needle support layer and a seal effecting recess extending into the micro-needle support layer for co-operating with the first membrane for sealing thereof with the active substance accommodating layer.

Preferably, the ones of the seal effecting projecting elements and the seal effecting recesses of the needle support layer are adapted to co-operate with corresponding ones of seal effecting projecting elements and seal effecting recesses formed in the first major surface of the active substance accommodating layer.

In another embodiment of the invention an activation cartridge comprising a plurality of activating means is provided for securing to the third membrane of the drive substance cartridge with the respective activating means aligned with the drive substance accommodating chambers.

Preferably, the third membrane is impermeable to the drive substance.

In one embodiment of the invention the second membranes of the respective active substance and drive substance cartridges are adapted to be bonded together.

In another embodiment of the invention the second membranes of the respective active substance and drive substance cartridges are adapted to be bonded together by one of adhesive bonding or ultrasonic welding.

Advantageously, the first membrane is selectively burstable adjacent the respective active substance accommodating chambers. Advantageously, a securing means is provided for securing the device to the skin of a subject.

The invention also provides a method for forming a delivery device from a kit of parts according to the invention, the method comprising securing the active substance cartridge to the drive cartridge with the respective second membranes of the active substance cartridge and the drive cartridge located between the active substance accommodating layer and the drive substance accommodating layer and with at least some of the drive substance accommodating chambers aligned with corresponding ones of the active substance accommodating chambers.

Preferably, the method further comprises securing the micro-needle element to the active substance cartridge with the first membrane located between the needle support layer and the active substance accommodating layer, and with at least some of the micro-needles aligned with corresponding ones of the active substance accommodating chambers.

Advantageously, the method further comprises securing the activation cartridge to the drive cartridge with the third membrane located between the drive substance accommodating layer and the activation cartridge, and with the activating means of the activation cartridge aligned with at least some of the drive substance accommodating chambers.

Further the invention provides a method for producing a delivery device in kit form for transferring a substance between the device and a subject, the method comprising providing an active substance cartridge comprising an active substance accommodating layer defining first and second opposite major surfaces and having a plurality of discrete active substance accommodating chambers extending through the active substance accommodating layer between the first and second major surfaces, and an active substance located in at least some of the active substance accommodating chambers, the active substance cartridge having a first membrane abutting and sealably secured to the first major surface of the active substance accommodating layer sealably closing the active substance accommodating chambers adjacent the first major surface thereof, and a second membrane abutting and sealably secured to the second major surface of the active substance accommodating layer sealably closing the active substance accommodating chambers adjacent the second major surface of the active substance accommodating layer, providing a drive cartridge for securing to the active substance cartridge, the drive cartridge comprising a drive substance accommodating layer defining opposite first and second major surfaces and having a plurality of discrete drive substance accommodating chambers extending into the drive substance accommodating layer from the first major surface thereof, at least some of the drive substance accommodating chambers being alignable with corresponding ones of the active substance accommodating chambers of the active substance cartridge, and a drive substance being provided in at least some of the drive substance accommodating chambers, the drive cartridge further comprising a second membrane abutting and sealably secured to the first major surface of the drive substance accommodating layer sealably closing the drive substance accommodating chambers adjacent the first major surface of the drive substance accommodating layer, and providing the drive cartridge to be securable to the active substance cartridge with the respective second membranes of the drive cartridge and the active substance cartridge abutting each other and located between the drive substance accommodating layer and the active substance accommodating layer, and with at least some of the drive substance accommodating chambers aligned with corresponding ones of the active substance accommodating chambers.

Preferably, the method further comprises providing a micro-needle element having a needle support layer and a plurality of micro-needles extending from the needle support layer, and providing the micro-needle element to be securable to the active substance cartridge with the first membrane located between the needle support layer and the active substance accommodating layer, and with at least some of the micro-needles aligned with corresponding ones of the active substance accommodating chambers.

Advantageously, each drive substance accommodating chamber extends from the first major surface of the drive substance accommodating layer to the second major surface of the drive substance accommodating layer, and the method further comprises sealably securing a third membrane to the second major surface of the drive substance accommodating layer for sealably closing the drive substance accommodating chambers adjacent the second major surface of the drive substance accommodating layer.

Preferably, the method further comprises providing an activation cartridge for securing to the drive cartridge, the activation cartridge having an activating means for co-operating with the drive substance in the respective drive substance accommodating chambers of the drive cartridge for causing the drive substance to expand, and providing the activation cartridge to be securable to the drive cartridge with the third membrane located between the drive substance accommodating layer and the activation cartridge, and with the activating means aligned with at least some of the drive substance accommodating chambers.

The invention also provides a method for moulding a micro-needle element from a mouldable material, the method comprising integrally moulding at least one micro-needle with and extending from a needle support layer in a mould, and moulding at least one first communicating means corresponding to the at least one micro-needle through the needle support layer adjacent the micro-needle during moulding of the micro-needle element, and moulding a second communicating means extending along an outer surface of each micro-needle during moulding of the micro-needle element with the second communicating means communicating with the first communicating means.

Preferably, a sealing means is moulded on the micro-needle support layer during moulding of the micro-needle element for sealing against the skin of a subject for preventing loss of a substance as the substance is passing from one of the first and second communicating means to the other.

Advantageously, the micro-needle element is moulded from a polymer material.

The advantages of the invention are many. By providing the transfer and delivery devices in kit form, the transfer and delivery devices become modular devices, which can be produced in a number of parts by different manufacturers with appropriate skills to manufacture each part, and the parts can then subsequently be assembled by a physician, a surgeon, a paramedic or the like. This, thus, permits a physician, surgeon or paramedic to select a pre-charged active substance cartridge which contains the active substance or active substances to be administered to the subject, and then to assemble the active substance cartridge with an appropriate drive substance cartridge and an activation cartridge, and where appropriate a micro-needle element is also assembled with the cartridges. Thus, a pharmaceutical company which has the expertise in handling pharmaceuticals may produce the active substance cartridge, while a manufacturer with expertise in the handling of drive substances could produce the drive substance cartridge. The activation cartridge typically would be produced by a manufacturer with electronics, computer and software skills.

By providing the transfer and delivery devices with micro-needles with channels recessed into the outer surface thereof, the transfer and delivery devices are particularly suitable for accommodating large molecule active substances, and where the transfer and delivery devices are to be used for withdrawing a sample of bodily fluid, the transfer and delivery devices are particularly suitable for withdrawing samples of bodily liquids of relatively large molecular size.

A further advantage of providing the micro-needles with channels recessed into the outer surface of the micro-needles is that coring is avoided, which can otherwise arise where a bore is provided through a micro-needle, whereby on being urged into the skin of the subject, a core of tissue may form in the bore of the micro-needle, thus leading to a blockage of the micro-needle. A further advantage of providing the micro-needle with channels, instead of bores is that the channel can be terminated short of the distal tip of the micro-needle, which thereby permits the micro-needle to be provided with a sharp penetrating distal pointed tip.

The provision of the means for effecting a seal between the respective layers and the adjacent membranes adjacent the active and drive substances accommodating chambers provides a particularly important advantage in that it avoids the risk of leakage of the active substance when the active substance is provided in liquid form from one active substance accommodating chamber to adjacent active substance accommodating chambers, and similarly, to micro-needles corresponding to adjacent active substance accommodating chambers. Additionally, the provision of the means for effecting a seal between the drive substance and the active substance accommodating chamber and the adjacent membrane avoids the risk of the active substance and the drive substance when they are provided in liquid form leaking into adjacent corresponding active substance accommodating chambers and adjacent corresponding drive substance accommodating chambers, as the case may be.

Figure 5:
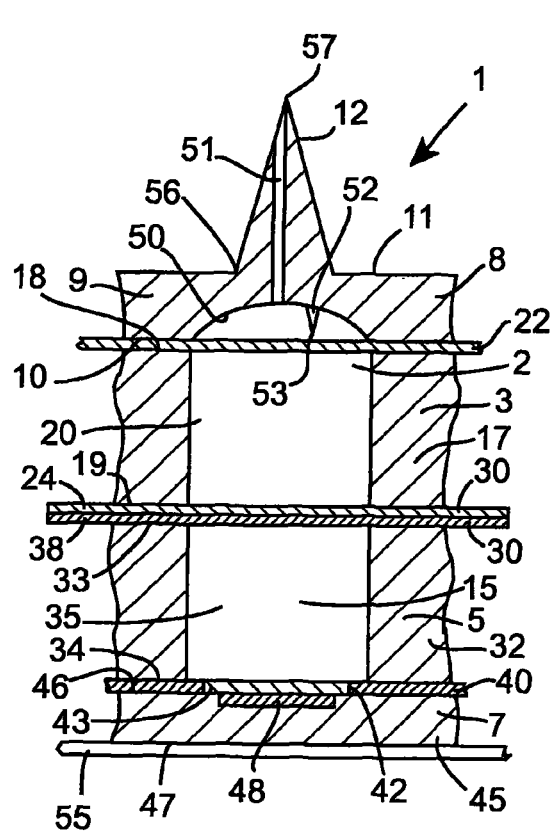
Figure 6:
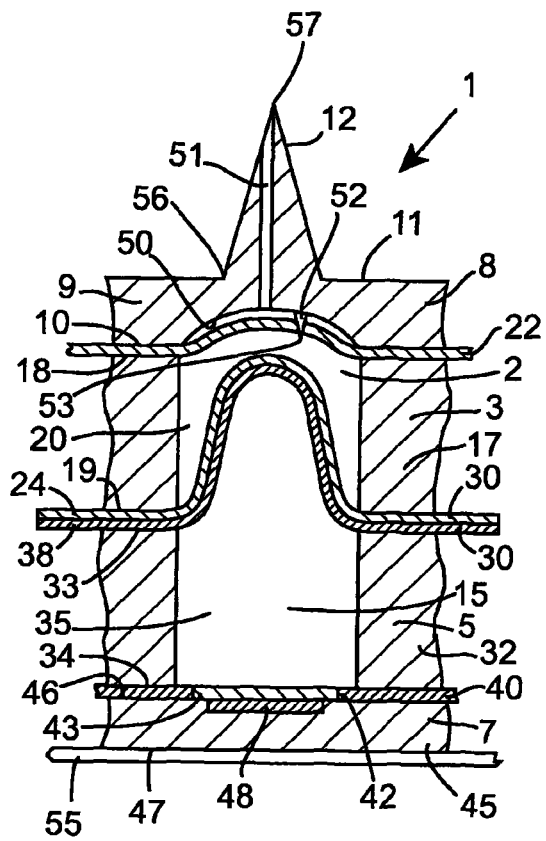
Figure 21:
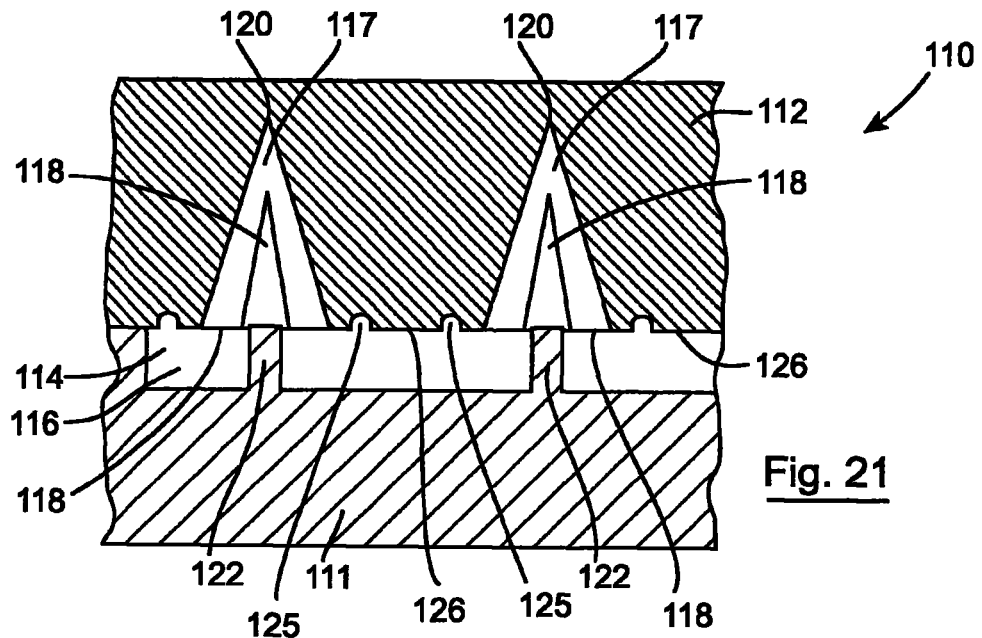
Figure 13:
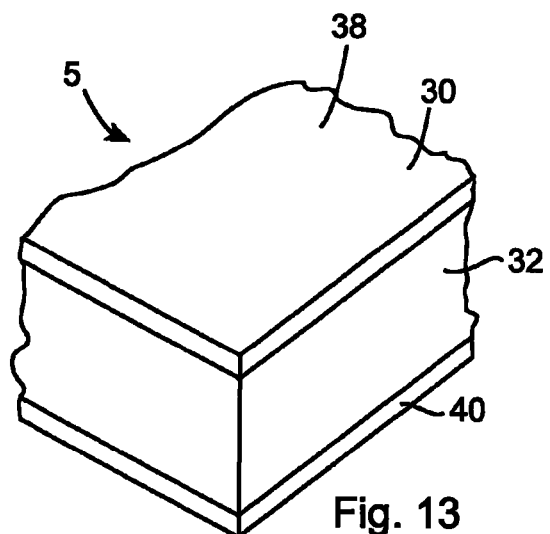
Figure 22:
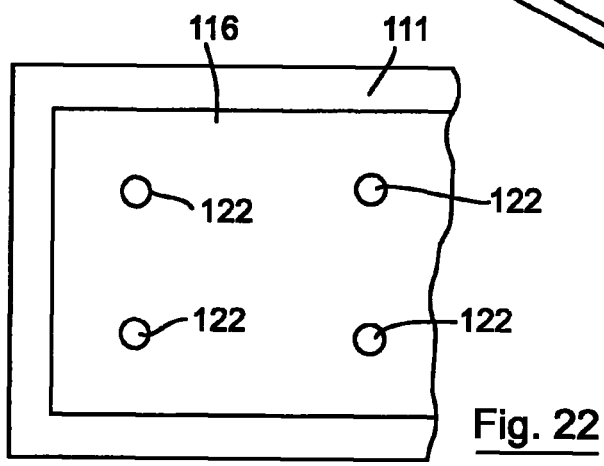
Figure 25:
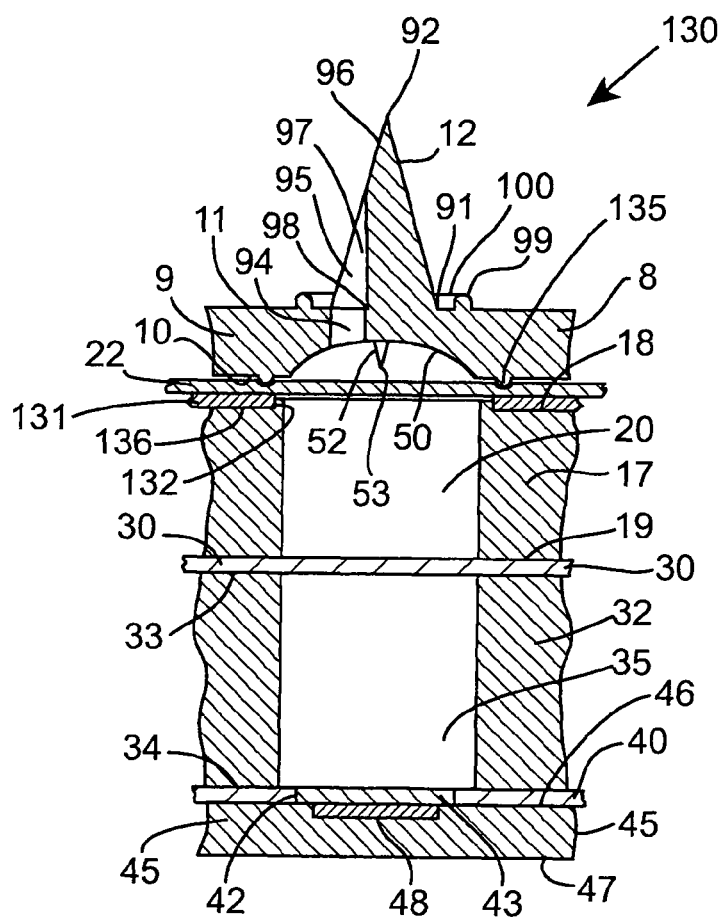
Figure 26:
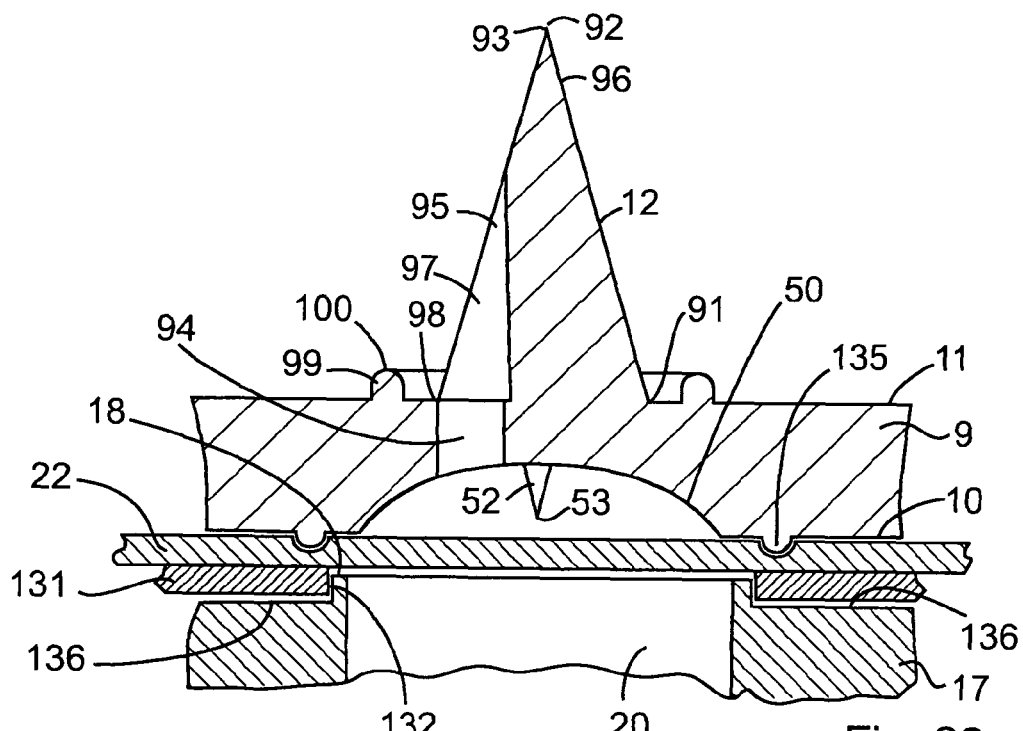
Figure 27:
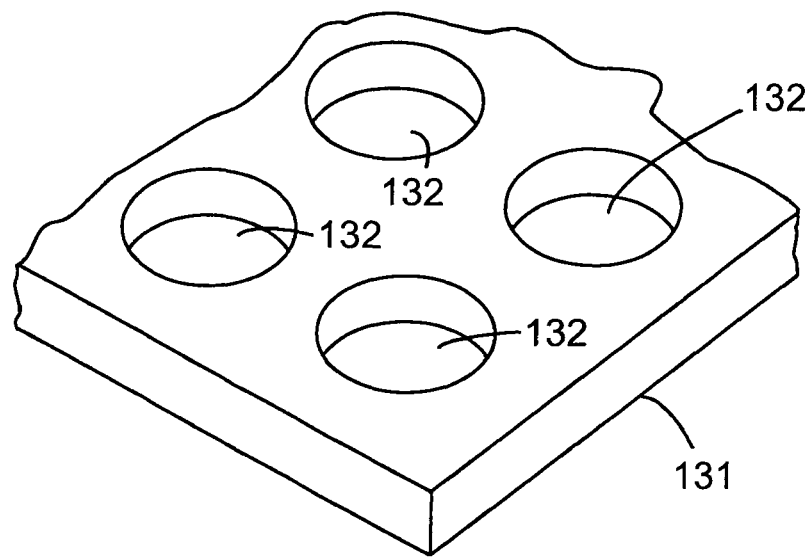
Figure 28:
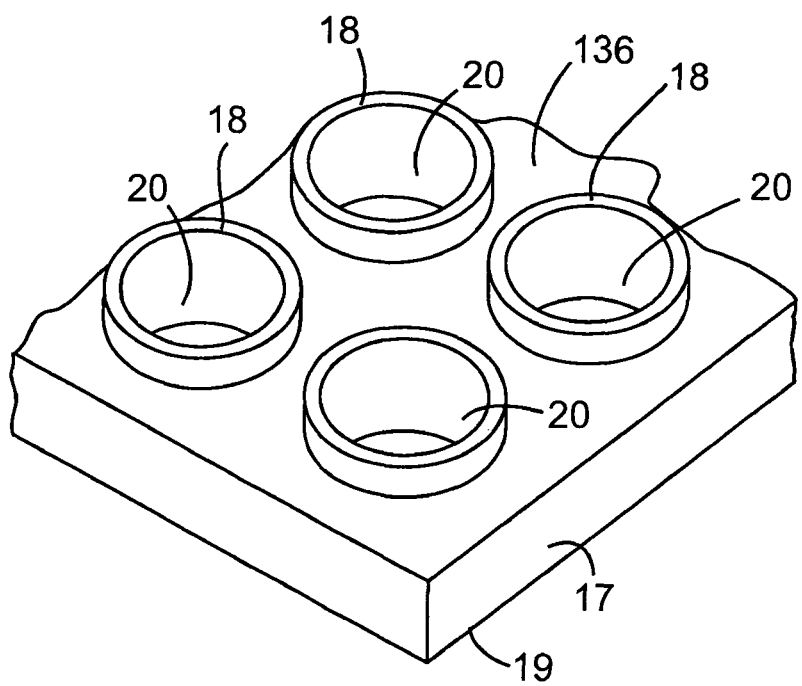

The invention will be more clearly understood from the following description of some preferred embodiments thereof, which are given by way of example only, with reference to the accompanying drawings, in which:

FIG. 1 is a side elevational view of a micro-needle delivery device according to the invention, FIG. 2 is a perspective view of a portion of an active substance cartridge also according to the invention of the micro-needle delivery device of FIG. 1, FIG. 3 is a perspective view of a portion of a drive substance cartridge also according to the invention of the micro-needle delivery device of FIG. 1, FIG. 4 is a perspective view of a portion of an activation cartridge of the micro-needle delivery device of FIG. 1, FIG. 5 is a transverse cross-sectional side elevational view of the micro-needle delivery device of FIG. 1 illustrating portions of the device in one state, FIG. 6 is a view similar to FIG. 5 of the micro-needle delivery device of FIG. 1 illustrating some of the portions of the micro-needle delivery device in a different state to that of FIG. 5, FIG. 7 is a view similar to FIG. 5 of a portion of a micro-needle delivery device according to another embodiment of the invention, FIG. 8 is a perspective view of a detail of the micro-needle delivery device of FIG. 7, FIG. 9 is a view similar to FIG. 5 of a portion of a micro-needle delivery device according to another embodiment of the invention, FIG. 10 is a view similar to FIG. 5 of a micro-needle delivery device according to a further embodiment of the invention, FIG. 11 is a side elevational view of a micro-needle delivery device according to another embodiment of the invention, FIG. 12 is a perspective view of a portion of an active substance cartridge also according to the invention of the micro-needle delivery device of FIG. 11, FIG. 13 is a perspective view of a portion of a drive substance cartridge also according to the invention of the micro-needle delivery device of FIG. 11, FIG. 14 is a transverse cross-sectional side elevational view of a portion of the micro-needle delivery device of FIG. 11, FIG. 15 is a view similar to FIG. 14 of the micro-needle delivery device of FIG. 11 illustrating portions of the micro-needle delivery device of FIG. 11 in a different state to that of FIG. 14, FIG. 16 is a perspective view of a portion of the micro-needle delivery device of FIG. 11, FIG. 17 is a side elevational view of a micro-needle delivery device according to another embodiment of the invention, FIG. 18 is a transverse cross-sectional end elevational view of the micro-needle delivery device of FIG. 17, FIG. 19 is a view similar to FIG. 18 of the micro-needle delivery device of FIG. 17 illustrating portions of the micro-needle delivery device in a different state to that of FIG. 18, FIG. 20 is a perspective view of a portion of the micro-needle delivery device of FIG. 17, FIG. 21 is a transverse cross-sectional side elevational view of a micro-mould according to the invention for moulding a micro-needle element of the micro-needle delivery device of FIG. 17, FIG. 22 is a top plan view of a portion of the micro-mould of FIG. 21, FIG. 23 is an underneath plan view of another portion of the micro-mould of FIG. 21, FIG. 24 is a side elevational view of a micro-needle delivery device according to another embodiment of the invention, FIG. 25 is a transverse cross-sectional end elevational view of a portion of the micro-needle delivery device of FIG. 24, FIG. 26 is an enlarged cross-sectional view of a detail of the portion of FIG. 25 of the micro-needle delivery device of FIG. 24, FIG. 27 is a perspective view of a portion of the micro-needle delivery device of FIG. 24, FIG. 28 is a perspective view of a detail of another portion of the micro-needle delivery device of FIG. 24, and FIG. 29 is a perspective view of another portion of the micro-needle delivery device of FIG. 24.

Referring to the drawings and initially to FIGS. 1 to 6, there is illustrated a transfer device, which in this case is a micro-needle delivery device according to the invention, indicated generally by the reference numeral 1, which is suitable for delivering an active substance 2 in liquid form transdermally, intradermally or subcutaneously to a subject. The active substance 2 may be a medicament, or any other active substance which it is desired to deliver to a subject. The micro-needle delivery device 1 in this embodiment of the invention is particularly suitable for providing in kit form, and may be provided as a kit of parts suitable for subsequent assembly by a physician, a surgeon or a paramedic. The kit of parts of the micro-needle delivery device 1 in this case comprises an active substance cartridge, which is also according to the invention and indicated generally by the reference numeral 3 for accommodating the active substance 2, a drive cartridge, which is also according to the invention, and indicated generally by the reference numeral 5, and an activation cartridge which is also according to the invention and indicated generally by the reference numeral 7. The kit of parts also comprises a micro-needle element indicated generally by the reference numeral 8. The micro-needle element 8 comprises a micro-needle support layer 9 defining a first major surface 10 and an opposite second major surface 11 and a plurality of micro-needles 12 extending from the second major surface 11 and configured on the micro-needle support layer 9 in a matrix.

The micro-needle element 8 is adapted to be secured to the active substance cartridge 3, and the drive substance cartridge 5 is also adapted to be secured to the active substance cartridge 3 with the active substance cartridge 3 located between the drive substance cartridge 5 and the micro-needle element 8. The activation cartridge 7 is adapted to be secured to the drive substance cartridge 5 with the drive substance cartridge 5 located between the active substance cartridge 3 and the activation cartridge 7. With the micro-needle delivery device 1 so assembled and attached to the skin of a subject with the micro-needles 12 penetrating the skin of the subject, a drive substance 15 in the drive substance cartridge 5 is expanded by the activation cartridge 7 so that expansion of the drive substance 15 in the drive substance cartridge 5 urges the active substance 2 in the active substance cartridge 3 through the micro-needles 12 of the micro-needle element 8 for transdermal or subcutaneous delivery to the subject as will be described below.

Turning initially to the active substance cartridge 3, the active substance cartridge 3 comprises a first layer, namely, an active substance accommodating layer 17 of a polymer material defining a first major surface 18 and an opposite second major surface 19. A plurality of discrete active substance accommodating chambers 20 extend through the active substance layer 17 between the first major surface 18 and the second major surface 19 for accommodating the active substance 2. The active substance accommodating chambers 20 are of circular transverse cross-section and are arranged in a matrix similar to the matrix in which the micro-needles 12 are arranged, and are alignable with respective corresponding ones of the micro-needles 12, one active substance accommodating chamber 20 being provided for each micro-needle 12. A first membrane 22 is sealably secured to the first major surface 18 of the active substance accommodating layer 17 for sealably closing the active substance accommodating chambers 20 adjacent the first major surface 18. A first one 24 of a pair of second membranes 30 is sealably secured to the second major surface 19 of the active substance accommodating layer 17 for sealably closing the active substance accommodating chambers 20 adjacent the second major surface 19.

The first membrane 22 is of a rupturable foil material and is rupturable in response to a build-up of pressure in the active substance 2 in the respective corresponding active substance accommodating chambers 20 for communicating the active substance accommodating chambers 20 with the corresponding micro-needles 12 for in turn accommodating the active substance from the active substance accommodating chambers 20 transdermally or subcutaneously to the subject. The foil of the first membrane 15 may be a metal foil or a polymer foil, or may be of a foil laminated with a plastics film, or may be of any other suitable burstable or rupturable material.

The first one 24 of the second membranes 30 is of a stretchable material suitable for expanding into the respective active substance accommodating chambers 20 in response to being urged therein by the drive substance cartridge 5 as will be described below. The first one 24 of the second membrane 30 is of a sufficiently stretchable material for expanding into the active substance accommodating chambers 20 as illustrated in FIG. 6, firstly, for increasing the pressure of the active substance 2 in the active substance accommodating chambers 20 to burst and rupture the first membrane 22, and secondly, for in turn urging the active substance 2 from the respective active substance accommodating chambers 20 through the corresponding micro-needles 12. In this embodiment of the invention the material of the first one 24 of the second membranes 30 is polyurethane.

Turning now to the drive substance cartridge 5, the drive substance cartridge 5 comprises a second layer, namely, a drive substance accommodating layer 32 of a polymer material defining a first major surface 33 and an opposite second major surface 34. A plurality of discrete drive substance accommodating chambers 35 extend through the drive substance accommodating layer 32 from the first major surface 33 thereof to the second major surface 34, and accommodate the drive substance 15 which is described below. The drive substance accommodating chambers 35 are of circular transverse cross-section and are arranged in a matrix similar to the matrix in which the active substance accommodating chambers 20 are arranged in the active substance accommodating layer 17, so that the drive substance accommodating chambers 35 are alignable with respective corresponding ones of the active substance accommodating chambers 20 when the drive substance cartridge 5 is assembled with the active substance cartridge 3. Additionally, the diameter of the drive substance accommodating chambers 35 is substantially similar to the diameter of the active substance accommodating chambers 20.

In this embodiment of the invention the drive substance 15 is provided in each of the drive substance accommodating chambers 35, and comprises an expandable substance which expands in response to an increase in temperature. In this particular embodiment of the invention the drive substance comprises a plurality of microspheres of the type which are supplied and sold under the Trade Mark EXPANCEL.

A second one 38 of the pair of second membranes 30 is sealably secured to the first major surface 33 of the drive substance accommodating layer 32 to sealably close the drive substance accommodating chambers 35 adjacent the first major surface 33. A third membrane 40 sealably secured to the second major surface 34 of the drive substance accommodating layer 32 sealably closes the drive substance accommodating chambers 35 adjacent the second major surface 34.

The second one 38 of the pair of second membranes 30 is of a stretchable material, which is similar to the stretchable material of the first one 24 of the second membranes 30, which is sealably secured to the active substance accommodating layer 17 of the active substance cartridge 5, so that when the drive substance cartridge 5 and the active substance cartridge 3 are assembled together with the two second membranes 30 abutting each other, expansion of the drive substance 15 in the drive substance accommodating chambers 35 results in the second membranes 30 being urged into the corresponding respective active substance accommodating chambers 20 for pressurising the active substance 2 therein, and for in turn urging the active substance 2 from the active substance accommodating chambers 20.

The third membrane 40 is provided with a plurality of discrete openings 42 aligned with the respective drive substance accommodating chambers 35. The openings 42 are sealably closed by heat transfer discs 43 of metal material for transferring heat, as will be described below, from the activation cartridge 7 to the drive substance 15 in the respective drive substance accommodating chambers 35. In this embodiment of the invention the third membrane 40 is of a heat insulating material for minimising heat transfer between adjacent heat transfer discs 43, and in turn, between adjacent drive substance accommodating chambers 35.

The activation cartridge 7 comprises an activating layer 45, and may be of polymer material having a first major surface 46 and an opposite second major surface 47, but more typically, the activating layer will be of a ceramics material or a material of the type from which a printed circuit board is formed. A plurality of activating means, namely, respective discrete and independently operable electrical heating elements 48 are formed on the first major surface 46 of the activating layer 45, and are arranged in a matrix and are alignable with the drive substance accommodating chambers 35 to co-operate with corresponding ones of the drive substance accommodating chambers 35 for raising the temperature of the drive substance 15 contained therein for expanding the drive substance. Each heating element 48 comprises a thin film resistive heating element which is formed on the activating layer 45 by a suitable forming process which will be well known to those skilled in the art. Each heating element 48 is individually powered from a power source (not shown), and an appropriately programmed microprocessor (not shown) is provided for selectively applying electrical power to the respective heating elements 48 as will be described below. Typically, the heating elements may be printed onto the first major surface 46 of the activating layer 45.

The power supply is supplied to the heating elements 48 through electrically conductive tracks (not shown) which are formed on the activating layer 45 by a suitable forming process which will be well known to those skilled in the art, for example, by printing. The microprocessor for controlling the power supply to the heating elements may be provided as a separate clip-on unit which may be clipped onto the activating layer 45, or may be integrally formed in the activating layer 45. The power supply in this embodiment of the invention is provided by one or more batteries, which may be provided to be clipped on to the activating layer 45, or alternatively, may be formed in some of the active substance accommodating chambers 20 or the drive substance accommodating chambers 35, or both by providing an electrolyte in the appropriate ones of the chambers 20 and/or 35 with corresponding electrodes located in the appropriate chambers 20 and/or 35. Power would be supplied to the heating elements 48 from the appropriate chambers 20 and/or 35 under the control of the microprocessor.

Returning now to the micro-needle element 8, the micro-needle support layer 9 is of a polymer material, and the micro-needles 12, also of polymer material, are integrally moulded with the micro-needle support layer 9. The micro-needles 12 are of conical shape tapering from a proximal end 56 adjacent the second major surface 11 of the micro-needle support layer 9 to a distal pointed tip 57. A communicating means for accommodating the active substance from the active substance accommodating chambers 20 through the micro-needles 12 comprises a first communicating means which is provided by a plurality of cavities 50 which extend into the first major surface 10 of the micro-needle layer 9 and a second communicating means provided by a plurality of communicating bores 51 extending from the respective cavities 50 through the corresponding micro-needles 12. The cavities 50 are arranged in the micro-needle support layer 9 in an array and are aligned with the micro-needles 12, and in turn are alignable with corresponding ones of the active substance accommodating chambers 20. In this embodiment of the invention the communicating bores 51 extend coaxially through the corresponding micro-needles 12.

A puncturing means, in this embodiment of the invention a puncturing member 52 extends from the micro-needle support layer 9 into each cavity 50 and terminates in a piercing point 53 for engaging and bursting the first membrane 22 on the first membrane 22 being urged into the corresponding cavity 50 under pressure of the active substance 2 in the corresponding one of the active substance accommodating chambers 20.

In use, in general, the active substance cartridge 3, the drive substance cartridge 5 and the activation cartridge 7, as well as the micro-needle element 8 may each be manufactured and supplied by different manufacturers, although, in certain cases, it is envisaged that the micro-needle element 8, the active substance accommodating layer 17 and the drive substance accommodating layer 32 may be manufactured by the same manufacturer, but may be formed into the respective cartridges separately. For example, it is envisaged that a pharmaceutical company may produce the active substance cartridges 3 by filling the active substance accommodating chambers 20 in the active substance accommodating layer 12 with the active substance 2 and sealing the active substance 2 in the active substance accommodating layer 17 by sealing the first and second membranes 22 and 24 to the first and second major surfaces 18 and 19 of the active substance accommodating layer 17.

The drive substance cartridges may be produced by a different supplier, who would fill the drive substance accommodating chambers 35 of the drive substance accommodating layer 32 with the drive substance 15, and seal the drive substance 15 into the drive substance accommodating chambers 35 by sealably securing the second membrane 38 and the third membrane 40 to the first and second major surfaces 33 and 34 of the drive substance accommodating layer 32.

The activation cartridge 7 may be manufactured and supplied by a firm with electronics and microprocessor expertise. The micro-needle element 8 typically would be supplied in a sterile pack, as would the active substance cartridge 3. The drive substance cartridge 5 and the activation cartridge 7 may also be supplied in a sterile pack, although this would not be essential.

A physician, surgeon or paramedic would then assemble the active substance cartridge 3, the drive substance cartridge 5, the activation cartridge 7 and the micro-needle element 8. When carrying out the assembly the physician, surgeon or paramedic would select an active substance cartridge 3 with the appropriate active substance 2 or active substances 2 in the active substance accommodating chambers 20, and typically, would also programme the microprocessor in the activation cartridge 7 to activate the heating elements 48 at appropriate times to discharge the active substance or substances 2 at appropriate time intervals over a treatment period. A treatment period, typically, may be a few days or a week. Thus, depending on the number of different active substances with which the active substance accommodating chambers 20 are charged, a subject may be treated with a number of active substances over a treatment period. The different active substances may be administered to the subject simultaneously or at different times over the treatment period.

During assembly, the cartridges and the micro-needle element 8 would be assembled with the active substance cartridge 3 located between the micro-needle element 8 and the drive substance cartridge 5, while the drive substance cartridge 5 would be located between the active substance cartridge 3 and the activation cartridge 7. The assembly may be secured together by bonding the respective cartridges to each other. However, more typically it will be secured together mechanically by a clamping arrangement. During assembly care would be taken to ensure that the micro-needles 12, the active substance accommodating chambers 20, the drive substance accommodating chambers 35 and the heating elements 48 are aligned with each other.

Alignment means may be provided for aligning the cartridges 3, 5 and 7 with each other and with the micro-needle element 8, and such alignment means may, for example, comprise short alignment projections, which would project from the major surfaces of the respective layers 9, 17, 32 and 45 to engage corresponding alignment recesses in the major surfaces of the adjacent layers 9, 17, 32 and 45.

Alternatively, a frame may be provided for accommodating the respective cartridges 3, 5 and 7 and the micro-needle element 8 therein.

A securing means for securing the micro-needle delivery device 1 to the skin of a subject may be provided by an adhesive patch 55 extending over the activation cartridge 7 and outwardly around the periphery thereof for bonding to the skin of the subject. Alternatively, a strap (not shown) may be secured to the activation cartridge 7 for extending around a limb of a subject onto which the micro-needle delivery device 1 is to be secured. Typically, where the micro-needle delivery device 1 is to be secured to one of the arms of a subject, the securing means would be provided by a strap, which would be extended around the arm of the subject and tightened onto the arm. Similarly, where the micro-needle delivery device 1 is to be secured to one of the legs of a subject, similarly, the securing means may be provided by a suitable strap. However, where it is not convenient to secure the micro-needle delivery device 1 to the subject by a strap, the adhesive patch 55 would be provided.

It will be appreciated that while the micro-needle delivery device 1 has been described as being supplied in kit form, it is envisaged that in certain cases the micro-needle delivery device 1 may be supplied as one single integral unit whereby the active substance accommodating chambers 20 would be charged with the active substance or substances 2 and the drive substance accommodating chambers 35 would be charged with the drive substances 15 by the same manufacturer, who would then assemble the micro-needle delivery device 1 and supply it as a single unit. In which case, it is envisaged that two second membranes 30 would not be required, and the second one 39 of the second membranes 30 could be omitted.

Referring now to FIGS. 7 and 8, there is illustrated a portion of a micro-needle delivery device according to another embodiment of the invention, indicated generally by the reference numeral 60, also for delivering an active substance 2 subcutaneously or transdermally to a subject. The micro-needle delivery device 60 is substantially similar to the micro-needle delivery device 1 and similar components are identified by the same reference numerals. The main difference between the micro-needle delivery device 60 and the micro-needle delivery device 1 is that firstly, the micro-needle delivery device 60 is supplied as a single unit, with the active substance cartridge 3, the drive substance cartridge 5 and the activation cartridge 7 as well as the micro-needle element 8 pre-assembled. Accordingly, only one second membrane 30 is required, namely, the first one 24 of the second membranes 30.

Secondly, in this embodiment of the invention a seal effecting means for effecting a seal between the first membrane 22 and the active substance accommodating layer 17 and the micro-needle support layer 9 adjacent the active substance accommodating chambers 20 is provided. A seal effecting means is also provided for effecting a seal between the second membrane 30 and the active substance accommodating layer 17 and the drive substance accommodating layer 32 adjacent the active substance accommodating chambers 20 and the drive substance accommodating chambers 35.

In this embodiment of the invention the seal effecting means for effecting a seal between the first membrane 22 and the adjacent layers 9 and 17 comprises a plurality of pairs of annular seal effecting projecting elements 61 and 62 which extend respectively from the first major surface 10 of the micro-needle support layer 9 and the first major surface 18 of the active substance accommodating layer 17. The annular seal effecting projecting elements 61 extend around and adjacent the cavities 50, while the annular seal effecting projecting elements 62 extend around and adjacent the corresponding active substance accommodating chambers 50. The annular seal effecting projecting elements 61 and 62 of the respective micro-needle support layer 9 and the active substance accommodating layer 17 are aligned with each other and co-operate to tightly engage and seal against the first membrane 22 for preventing leakage of the active substance from one active substance accommodating chamber 20 to adjacent active substance accommodating chambers 20 and to cavities 50 corresponding to adjacent active substance accommodating chambers 20.

The means for effecting a seal between the second membrane 30 and the active substance accommodating layer 17 and the drive substance accommodating layer 32 adjacent the active substance accommodating chambers 20 and the drive substance accommodating chambers 35 is provided by a plurality of pairs of annular seal effecting projecting elements 63 and 64 projecting respectively from the second major surface 19 of the active substance accommodating layer 17 and the first major surface 33 of the drive substance accommodating layer 32. The annular seal effecting projecting elements 63 extend around and adjacent corresponding ones of the active substance accommodating chambers 20, while the annular seal effecting projecting elements 64 extend around and adjacent the corresponding ones of the drive substance accommodating chambers 35. The action of the annular seal effecting projecting elements 63 and 64 on the second membrane 30 is similar to the action of the annular seal effecting projecting elements 61 and 62 on the first membrane 22. The annular seal effecting projecting elements 63 and 64 are aligned with each other and co-operate to tightly and sealably engage the second membrane 30 therebetween for effecting a seal therewith in order to prevent leakage of the active substance 2 and the drive substance 15 from the active substance accommodating chambers 20 and the drive substance accommodating chambers 35, respectively, to adjacent active substance accommodating chambers 20 and adjacent drive substance accommodating chambers 35.

Each annular seal effecting projecting element 61, 62, 63 and 64 is of ridge type cross-section terminating in a radiused membrane abutting the surface 65. In this embodiment of the invention the micro-needle element 8, the active substance accommodating layer 17, the drive substance accommodating layer 32 and the activation layer 45 are clamped together in order to effect adequate sealing between the annular seal effecting projecting elements 61 and 62 and the first membrane 22 and the annular seal effecting projecting elements 63 and 64 and the second membrane 30.

While the means for effecting a seal between the first membrane 22 and the micro-needle support layer 9 and the active substance accommodating layer 17 and for effecting a seal between the second membrane 30 and the active substance accommodating layer 17 and the drive substance accommodating layer 32, it is envisaged that one of the seal effecting projecting elements of the pairs of seal effecting projections 61 and 62 and one of the seal effecting projecting elements of the pairs of seal effecting projecting elements 63 and 64 may be omitted and replaced by an annular seal effecting recess which would co-operate with the corresponding one of the pair of seal effecting projecting elements for engaging the corresponding one of the first and second membranes 22 and 30 between the seal effecting projecting elements and the seal effecting recess.

Referring now to FIG. 9, there is illustrated a portion of a micro-needle delivery device according to another embodiment of the invention, indicated by the reference numeral 66. The micro-needle delivery device 66 is substantially similar to the micro-needle device 60, and similar components are identified by the same reference numerals. The only difference between the micro-needle delivery device 66 and the micro-needle delivery device 60 is that instead of providing the annular seal effecting projecting element 61 and 62 and 63 and 64 in pairs, in this embodiment of the invention only one of the seal effecting projecting elements of the respective pairs is provided. The annular seal effecting projecting elements 61 are provided extending from the first major surface 10 of the micro-needle layer 9 for engaging and tightly sealing the first membrane 22 against the first major surface 18 of the active substance accommodating layer 17. The annular seal effecting projecting elements 64 are provided on the drive substance accommodating layer 32 extending from the first major surface 33 thereof. The annular seal effecting projecting elements 64 engage the second membrane 30 and urge the second membrane 30 into tight sealing engagement with the second major surface 19 of the active substance accommodating layer 17.

It is believed that in many cases the provision of the annular seal effecting projecting elements 61 and 63 extending from the micro-needle support layer 9 and the drive substance accommodating layer 32 will be sufficient for effecting a suitable seal between the first membrane 22 and the micro-needle support layer 9 and the active substance accommodating layer 17, and between the second membrane 30 and the active substance accommodating layer 17 and the drive substance accommodating layer 32.

Referring now to FIG. 10, there is illustrated a micro-needle delivery device according to another embodiment of the invention, indicated generally by the reference numeral 70, also for delivering an active substance 2 to a subject transdermally or subcutaneously. The micro-needle delivery device 70 is substantially similar to the micro-needle delivery devices 1 and 60, and similar components are identified by the same reference numerals. In this embodiment of the invention the micro-needle delivery device 70 is suitable for supplying in kit form and comprises a micro-needle element 8, an active substance cartridge 3, a drive substance cartridge 5 and an activation cartridge 7. Additionally, in this embodiment of the invention the means for effecting a seal between the first membrane 22 and the micro-needle support layer 9 and the active substance accommodating layer 17 adjacent the cavities 50 and the active substance accommodating chambers 20, and in this case, is provided by a plurality of tapering annular seal effecting projecting elements 71 extending from the first major surface 10 of the micro-needle support layer 9 which engage corresponding annular seal effecting recesses 72 extending into the active substance accommodating layer 17 around and within the active substance accommodating chambers 20 adjacent the first major surface 10 of the micro-needle support layer 9.

The seal effecting projecting elements 71 extend from the first major surface 10 of the micro-needle support layer 9 around the corresponding ones of the cavities 50 and taper inwardly. The active substance accommodating chambers 20 taper inwardly from the first major surface 18 to the second major surface 19 of the active substance accommodating layer 17, so that the portion of the active substance accommodating chambers 20 adjacent the first major surface 18 effectively form the seal effecting recesses 72. The tapering angle of the seal effecting projecting elements 71 is similar to the tapering angle of the seal effecting recesses 72 for tightly and sealably engaging the first membrane 22 between circumferential surfaces 73 and 74 of the seal effecting projecting elements 71 and seal effecting recesses 72, respectively.

A means for effecting a seal between the first and second ones 24 and 38 of the pair of second membranes 30 and the second major surface 19 of the active substance accommodating layer 17 and the first major surface 33 of the drive substance accommodating layer 32 adjacent the active and drive substance accommodating chambers 20 and 35 also comprise tapering annular seal effecting projecting elements 75 which extend from the second major surface 18 of the active substance accommodating layer 17 for engaging corresponding annular seal effecting recesses 76 formed into the first major surface 33 of the drive substance accommodating layer 32 within the drive substance accommodating chambers 35. The drive substance accommodating chambers 35 taper inwardly from the first major surface 33 to the second major surface 34 of the drive substance accommodating layer 32, and the seal effecting projecting elements 75 taper correspondingly from the second major surface 19 of the active substance accommodating layer 17. The sealing effect of the seal effecting projecting elements 75 and the seal effecting recesses 76 on the second membranes 30 is similar to the effect of the seal effecting projecting elements 71 and the seal effecting recesses 72 on the first membrane 22.

Additionally, in this embodiment of the invention the communicating bore 51 extending through each micro-needle 12 is offset from the central axis of the micro-needle 12, thereby permitting the distal pointed tip 57 of the micro-needle 12 to be provided with a sharp skin penetrating point. The provision of the slightly offset bore also minimises coring of tissue in the communicating bore 51, which otherwise would lead to blockages of the communicating bores 51.

Referring now to FIGS. 11 to 16, there is illustrated a delivery device according to another embodiment of the invention, indicated generally by the reference numeral 80. The delivery device 80 is somewhat similar to the micro-needle delivery device 1, and similar components are identified by the same reference numerals. The delivery device 80 is also suitable for supplying in kit form. The main difference between the delivery device 80 and the micro-needle delivery device 1 is that the micro-needle element 8 has been omitted.

In this embodiment of the invention the active substance 2 is located in the active substance accommodating chambers 20, but instead of being in liquid form, the active substance 2 is contained in solid form structures 81 which are located in the active substance accommodating chambers 20. Each solid form structure 81 comprises a base element 82 and a conical element 83 extending from the base element 82. The conical element 83 terminates in a pointed tip 85 which is adapted for penetrating the skin of the subject.

Each solid form structure 81 is located in a corresponding one of the active substance accommodating chambers 20 with the pointed tip 85 located adjacent the first membrane 22, so that on activation of the drive substance 15 in the corresponding drive substance accommodating chamber 35 by the corresponding heating element 48, the solid form structure 81 is urged outwardly of the corresponding active substance accommodating chamber 20 by the action of the drive substance on the two second membranes 30. The urging action of the second membranes 30 on the solid form structures 81 result in the pointed tips 81 thereof penetrating, and thus rupturing the first membrane 22 and in turn penetrating the skin of the subject when the delivery device 80 is secured to the subject.

The solid form structures 81 may be constructed as lattice type structures which may or may not be of a material which would be biodegradable within the skin of the subject. The lattice form structure would be impregnated with the active substance. Typically, the active substance would be located closer to the tip 85 of the solid form structure 81. Alternatively, the active substance may constitute the entire solid form structure. In another alternative embodiment of the invention the solid form structures 81 may comprise only the active substance and an excipient which would typically be mixed together with an appropriate binder so that the mixture of the active substance, excipient and the binder would set to form the solid form structure. In which case, a lattice form structure to support the solid form structure 81 would not be required.

The solid form structure comprising the active substance may be in the form of a sphere with a roughened surface. It is believed that such a solid form structure in the form of a sphere of relatively small diameter would penetrate the skin of a subject under the driving force exerted by the drive substance in the corresponding drive substance accommodating chamber 35. Roughening the surface of the sphere would further assist penetration of the skin of the subject by the sphere. Additionally, roughening of the surface of the sphere would also assist in bursting of the first membrane 22 by the sphere under the driving force of the drive substance in the corresponding drive substance accommodating chamber 35. Needless to say, the solid form structure comprising the active substance may be of any other suitable three-dimensional shape, for example, parallelepiped, or any other such shape, with or without a roughened surface.

In this embodiment of the invention the delivery device is supplied in kit form as three separate cartridges, namely, the active substance cartridge 3, the drive substance cartridge 5 and the activation cartridge 7, for subsequent assembly by a physician, surgeon or paramedic. The active substance cartridge 3 comprises the active substance accommodating layer 17 with the solid form structures 81 containing the active substance 2 located in the respective active substance accommodating chambers 20. The first membrane 22 is sealably secured to the first major surface 18 of the active substance accommodating layer 17, and the first one 24 of the second membranes 30 sealably secured to the second major surface 19 of the active substance accommodating layer 17.

The drive substance cartridge 5 comprises the drive substance accommodating layer 32 with the drive substance 15 located in the respective drive substance accommodating chambers 35. The second one 38 of the second membranes 30 is sealably secured to the first major surface 33 of the drive substance accommodating layer 32, and the third membrane 40 is sealably secured to the second major surface 34 of the drive substance accommodating chambers 35. The activation cartridge 7 is provided in the form already described with reference to the micro-needle device 1 of FIGS. 1 to 6.

It is envisaged that the delivery device 80 may be provided with means for effecting a seal between the second membranes 30 and the adjacent second major surface 19 of the active substance accommodating layer 17 and the first major surface 33 of the drive substance accommodating layer 32. Such means for effecting the seal may be provided by annular seal effecting projecting elements and/or annular seal effecting recesses of the types described with reference to the micro-needle devices 60 and 70.

Referring now to FIGS. 17 to 20, there is illustrated a micro-needle delivery device according to another embodiment of the invention, indicated generally by the reference numeral 90. In this embodiment of the invention the active substance 2 is provided in liquid form in the respective active substance accommodating chambers 20. The micro-needle delivery device 90 is substantially similar to the micro-needle delivery device 1, and similar components are identified by the same reference numerals. However, the micro-needle delivery device 90 differs from the micro-needle delivery device 1 in that firstly, the micro-needle delivery device 90 is provided pre-assembled as a single integral unit, and is thus not provided in kit form, and secondly, the micro-needles 12 and the micro-needle element 8 differ from the micro-needles 12 and the micro-needle element 8 of the micro-needle delivery device 1.

In this embodiment of the invention each micro-needle 12 is of conical shape and extends from a proximal end 91 adjacent the second major surface 11 of the micro-needle support layer 9 to a distal end 92 where the micro-needle 12 terminates in a pointed tip 93. A plurality of first communicating means provided by respective first communicating bores 94 extend through the micro-needle support layer 9 from the respective cavities 50 to the second major surface 11 adjacent the proximal end 91 of the respective micro-needles 12 for accommodating the active substance from the active substance accommodating chambers 20 through the micro-needle support layer 9 to the corresponding ones of the micro-needles 12.

A second communicating means provided by an elongated fluid accommodating channel 95 extends along an outer surface 96 of each micro-needle 12 and communicates with the corresponding first communicating bore 94 for accommodating the active substance from the corresponding first communicating bore 94 along the micro-needle 12 for delivering the active substance transdermally or subcutaneously to the subject. The fluid accommodating channel 95 of each micro-needle 12 is formed by a recess 97 which is formed into the outer surface 96 of the corresponding micro-needle 12. Each recess 97 is of partly circular transverse cross-section and tapers from the proximal end 91 towards the distal end 92 of the corresponding micro-needle 12. The recesses 97 terminate adjacent but spaced apart from the distal ends 92 of the respective micro-needles 12. Each recess 97 defines a partly circular area 98 on the second major surface 11 of the micro-needle support layer 9 adjacent the proximal end 91 of the corresponding micro-needle 12 from which the corresponding first communicating bore 94 extends into the micro-needle support layer 4.

A sealing means comprising an annular ridge type sealing element 99 extends from the second major surface 11 of the micro-needle support layer 9 adjacent each micro-needle 12 and extends around the micro-needle 12 for sealably engaging the skin of the subject in order to minimise, and in general, prevent leakage of the active substance 2 between the micro-needle support layer 9 and the skin of the subject as the active substance 2 passes from the corresponding first communicating bore 94 to the fluid accommodating channel 95 in the corresponding micro-needle 12 for transdermal, intradermal or subcutaneous delivery to the subject. Each ridge type sealing element 99 terminates in a radiused convex skin abutting surface 100 for sealably engaging against the skin of a subject. The height of each ridge type element 99 above the second major surface 11 of the micro-needle support layer 9 is relatively small, and is just sufficient to slightly distort the skin of the subject, sufficient to obtain a seal with the skin of the subject. Typically, the height of the ridge type element 99 above the second major surface 11 of the micro-needle support layer 9 would be in the order of 1 mm.

The annular ridge type sealing elements 99 by forming a seal with the skin of the subject minimise, and in general, prevent leakage of the active substance 2 between the skin of the subject and the micro-needle support layer 9 as the active substance passes from the corresponding fluid accommodating bore 94 in the micro-needle support layer 9 to the fluid accommodating channel 95 in the corresponding micro-needle 9.

Use of the micro-needle device 90 is similar to that of the micro-needle device 1. The active substance accommodating chambers 20 may be charged with the same active substance 2 or different active substances 2. Depending on the type or types of active substances 2 in the active substance accommodating chambers 20, the microprocessor (not shown) of the activating layer 45 will be appropriately programmed to sequentially operate the heating elements 48 in groups or individually at appropriate times over a predefined treatment regime during which the one or more active substances in the active substance accommodating chambers 20 are to be periodically delivered to the subject.

Referring now to FIGS. 21 to 23, there is illustrated a mould 110 also according to the invention for injection micro-moulding the micro-needle element 8 from a polymer material. The mould 110 is a two-part mould comprising a first part 111 and a second part 112. The first and second parts 111 and 112 when urged together define a mould cavity 114 within which the micro-needle element 8 is moulded. The mould cavity 114 is formed by a main cavity 116 which is formed in the first part 111 and which defines the micro-needle support layer 9. A plurality of secondary cavities 117 are formed in the second part 112 of the mould 110 and define the micro-needles 12. Each secondary cavity 117 communicates with the main cavity 116. Elongated tapering projections 118 of partly circular transverse cross-section extend into the respective secondary cavities 117 along side walls thereof from a proximal end 119 of the secondary cavity 117 towards but spaced apart from a distal end 120 for forming the fluid accommodating channels 95 in the respective micro-needles 12.

A plurality of core pins 122 extend into the main cavity 116 from the second part 112 of the mould 110, and are aligned with the corresponding projections 118 for forming corresponding ones of the first communicating bores 94 aligned with the corresponding fluid accommodating channels 95.

A plurality of annular grooves 125 extending into a surface 126 around corresponding respective ones of the secondary cavities 117 define the annular ridge type sealing elements 99 on the second major surface 11 of the micro-needle support layer 9.

Although the surface 126 of the first part 111 of the mould 110 has not been illustrated for forming the dome shaped cavities 50 and the puncturing members 52, the working of such a mould to form such dome shaped cavities 50 and puncturing members 52 in the micro-needle support layer 9 will be well known to those skilled in the art.

The advantages of the micro-needle device 90 according to this embodiment of the invention are many. Firstly, the micro-needle device 90 is suitable for delivering active substance of relatively large molecular weight transdermally, intradermally or subcutaneously to a subject. Secondly, the micro-needle element 8 of the micro-needle device 90 can be manufactured relatively simply and easily at relatively low cost with a relatively uncomplex injection mould. By virtue of the fact that the fluid accommodating channels 95 are provided by recesses extending into the outer surface of the micro-needles, the transverse cross-section of the fluid accommodating channels 95 may be of any desired cross-section. Furthermore, by virtue of the fact that the fluid accommodating channels are formed on the outer surface of the micro-needles, the fluid accommodating channel of each micro-needle may be formed to extend into the micro-needle to a relatively large depth, and additionally, the fluid accommodating channel may be formed to be of a relatively wide width. Thirdly, since the fluid accommodating channels are formed on the outer surface of the micro-needle, there is no requirement for a bore to extend through the micro-needle, and accordingly, each micro-needle can terminate in a sharply pointed tip in order to facilitate puncturing of the skin of the subject with minimum discomfort.

Fourthly, by virtue of the fact that the fluid accommodating channels are formed on the outer surface of the micro-needles, there is no need for core pins in a mould to form an elongated bore extending through the micro-needles. All that is required is the projection 118 correspondingly shaped extending from the side wall of each secondary cavity of the mould which defines the fluid accommodating channel.

Since the only bores which are required are those which form the first communicating bores 94 through the micro-needle support layer 9, and since there is no great limitation on the maximum diameter of these bores, and further, since the first communicating bores 94 are relatively short, the core pins 122 can likewise be correspondingly short and of a reasonable diameter. Therefore, there is little or no danger of the core pins breaking during ejection of the micro-needle element 8 from the mould.

While the micro-needle delivery device 90 has been described for delivering an active substance transdermally, intradermally and subcutaneously into a subject, it is envisaged that the micro-needle delivery device 90 may be provided for withdrawing a fluid sample of bodily fluid from a subject. In which case, the active substance accommodating chambers 20 would be adapted for receiving the fluid sample, and the drive substance in the respective drive substance accommodating chambers would be of a type which contracts instead of expands for withdrawing the second membrane, which initially would extend into the active substance accommodating chambers 20, from the active substance accommodating chambers 20, in order to draw a vacuum in the active substance accommodating chambers 20, for in turn drawing the fluid sample from the subject into the active substance accommodating chambers.

It is envisaged that the micro-needle device 90 may also be provided in kit form as described with reference to FIGS. 17 to 20, and in which case, a pair of second membranes 30, namely, the first one 24 and the second one 38 would be provided between the active substance accommodating layer 19 and the drive substance accommodating layer 32. Thus, the micro-needle device 90 could be supplied in kit form as already described with reference to FIGS. 1 to 6 and FIGS. 11 to 16.

While each sealing means of the micro-needle device 90 for sealing the micro-needle support layer 9 against the skin of a subject has been described as comprising annular ridge type sealing elements 99 extending around the corresponding micro-needle, any other suitable sealing means may be provided. For example, the ridge type sealing elements instead of terminating in a radiused convex skin abutting surface, could in fact terminate in an apex, whereby opposite sides of the annular ridge type sealing element would converge towards a ridge to form the apex.

It is also envisaged that the sealing means instead of extending completely around the corresponding micro-needle, the sealing means may extend partly around the corresponding first communicating bore which extends through the micro-needle support layer, and the sealing means would terminate at respective opposite sides of the first communicating bore in the micro-needle adjacent the proximal end thereof, and preferably, on respective opposite sides of the fluid accommodating channel of that micro-needle. Alternatively, the sealing means may be provided by a groove formed into the second major surface in the micro-needle support layer and extending around the corresponding micro-needle which would be adapted to receive a corresponding O-ring seal.

Indeed, in certain cases, the sealing means of the micro-needle device 90 for sealing the micro-needle support layer 9 against the skin of the subject may be provided by an annular piece of double sided adhesive sheet material, or single sided adhesive sheet material which would be located on the second major surface of the micro-needle support layer and extend around the corresponding micro-needle. One of the adhesive surfaces would be used for bonding the double sided adhesive material to the second major surface of the micro-needle support layer, and the other side where the material is double sided adhesive would be used for bonding the material to the skin of the subject. In which case, it is envisaged that the adhesive surface for bonding the material to the skin of the subject would initially be provided with a peelable releasable adhesive protective sheet.

It is further envisaged that the sealing means of the micro-needle device 90 may be provided by a sheet of material which would be bonded to the second major surface of the micro-needle support layer, and which would be provided with a plurality of openings for accommodating the micro-needles therethrough. The openings for accommodating the micro-needles therethrough would be sized to facilitate communication between the fluid accommodating channel of the corresponding micro-needle and the corresponding first communicating bore extending through the micro-needle support layer. When the sealing means is provided by a sheet of material bonded to the micro-needle support layer having a plurality of micro-needle accommodating openings extending therethrough, it is envisaged that the outer surface of the sealing material may be coated with an adhesive for bonding to the skin of the subject. In which case, it is envisaged that a peelable releasable protective sheet will be provided over the adhesive surface which would be removed prior to applying the micro-needle device to the skin of the subject.

In general, where the sealing means of the micro-needle device 90 is provided by a sheet of material bonded to the second major surface of the micro-needle support layer or such material formed into an annular seal extending around the corresponding micro-needle and bonded to the second major surface of the micro-needle support layer, it is envisaged that the material would be a resiliently deformable material or a relatively soft deformable material.

Referring now to FIGS. 24 to 28, there is illustrated a portion of a micro-needle device according to another embodiment of the invention, indicated generally by the reference numeral 130. The micro-needle device 130 is substantially similar to the micro-needle device 90 described with reference to FIGS. 17 to 20 and similar components are identified by the same reference numerals. The only difference between the micro-needle device 130 and the micro-needle device 90 is that a means for effecting a seal between the first major surface 10 of the active substance accommodating layer 17 and the first membrane 22 is provided by a gasket 131 located between the first membrane 22 and the active substance accommodating layer 17. The gasket 131 comprises a sheet of gasket material, which in this embodiment of the invention is silicone material, and is provided with a plurality of openings 132 extending through the gasket 131 at locations adjacent the active substance accommodating chambers 20 to accommodate the active substance from the active substance accommodating chambers 20 to the corresponding cavities 50 in the micro-needle support layer 9 when respective portions of the first membrane 22 have been ruptured to establish communication between the active substance accommodating chambers 20 and the corresponding cavities 50. The diameter of the openings 131 is substantially similar to the diameter of the active substance accommodating chambers 20. The sheet material of the gasket 131 is of thickness of approximately 0.3 mm.

Additionally, in this embodiment of the invention annular seal effecting projecting elements 135 extend from the first major surface 10 of the micro-needle support layer 9 around the respective cavities 50, and co-operate with corresponding annular seal effecting recesses 136 formed in the first major surface 18 of the active substance accommodating layer 17 around the corresponding active substance accommodating chambers 20 for sealably urging the first membrane 22 into tight sealing engagement with the gasket 131, and in turn for urging the gasket 131 into tight sealing engagement with the corresponding annular seal effecting recesses 136 in the active substance accommodating layer 17, thereby sealing the active substance accommodating chambers 20 adjacent the first major surface 18 of the active substance accommodating layer 17. The engaging action of the annular seal effecting projecting elements 135 on the first membrane 22 forms a liquid tight seal, thereby sealing the first membrane 22 against the micro-needle support layer 9.

It is also envisaged that in certain cases a gasket similar to the gasket 131 may be located between the active substance accommodating layer 17 and the second membrane 30, and further, it is envisaged that a gasket similar to the gasket 131 may be located between the first major surface 33 of the drive substance accommodating layer 32 and the adjacent second membrane 30, as the case may be, depending on whether the micro-needle device according to this embodiment of the invention is being supplied as a single pre-assembled unit or in kit form for subsequent assembly.

While the activating means of the micro-needle delivery devices, which have been described, have been described as comprising heating elements, any other suitable activating means besides heating elements may be provided. In certain cases, it is envisaged that the activating means may be a device for cooling the drive substance.

It will also be appreciated that while the drive substance has been described as being an EXPANCEL material, which comprising gas filled microspheres, gas filled microspheres sold under other Trade Marks may be used, and needless to say, other suitable drive substances may be used, for example, the drive substance may be a gas, or may be provided by a liquid which rapidly transitions from the liquid phase to the gaseous phase on being heated, alternatively, the drive substance may be provided by a porous polymer impregnated with a gas, which on being heated would either cause the polymer material to rapidly expand, or cause the gas to migrate from the porous polymer material as it expanded, for in turn, urging the second membrane into the corresponding active substance accommodating chambers.

It will be appreciated that while the micro-needle delivery devices have been described for delivering a liquid medicament into a subject, the micro-needle delivery devices may be used for delivering any suitable medicament, whether in liquid or gaseous form into a subject.

It is also envisaged that while the micro-needle delivery devices have been described as comprising puncturing members, the puncturing members may be omitted, and in which case, the first membrane would be of a material which would burst on pressure being applied to the active substance by the drive substance.

While the active substance and drive substance accommodating layers have been described and illustrated as being of similar thickness, the thickness of the active and drive substance accommodating layers may be the same or different. Indeed, in certain cases, it is envisaged that the drive substance accommodating layer may be thinner than the active substance accommodating layer or vice versa, and this would largely depend on the type of drive substance being used. Where gas filled spheres of the type sold under EXPANCEL are provided as the drive substance, since such gas filled spheres can expand up to four times and more their normal size, it is envisaged that the thickness of the drive substance accommodating layer may be less than the thickness of the active substance accommodating layer.

Additionally, while the active and drive substances accommodating chambers have been described as being of circular transverse cross-section, the active and drive substances accommodating chambers may be of any desired cross-section.

While specific dimensions of the respective layers, membranes and chambers have been described, it will be apparent to those skilled in the art that while the devices described are of micro-dimensions, the dimensions of the layers, chambers, membranes and micro-needles may vary. For example, it is envisaged that the thickness of the drive substance accommodating layer may be different to the thickness of the active substance accommodating layer, and while in general, it is envisaged that the diameters of the active substance accommodating chambers and the drive substance accommodating chambers will be similar, in certain cases, they may differ. It is also envisaged that a number of drive substance accommodating chambers may be provided for each single active substance accommodating chamber, and vice versa. Similarly, it is envisaged that a number of micro-needles may be provided for each active substance accommodating chamber, and in certain cases, it is envisaged that a plurality of active substance accommodating chambers may be provided for one of the micro-needles.

In general, it is envisaged that the micro-needle support layer will be of thickness in the range of 1 mm to 2 mm, the active substance accommodating layer will be of thickness in the range of 1 mm to 3 mm, and the drive substance accommodating layer may be of thickness in the range of 1 mm to 2 mm. It is also envisaged that the micro-needles may be of axial length in the range of 0.1 mm to 1 mm, and while in general, the micro-needles will taper at a cone angle of approximately 15°, it is envisaged that the micro-needles may be provided with a cone angle in the range of 15° to 45°.

In general, the active substance and drive substance accommodating chambers will be of circular transverse cross-section, although the cross-section of the active substance and drive substance accommodating chambers may be of any suitable or desired cross-section, for example, square cross-section, polygonal cross-section, such as, for example, triangular, hexagonal, octagonal, or indeed rectangular. In general, it is envisaged that where the active substance and drive substance accommodating chambers are provided of circular transverse cross-section, the diameter of the active substance and drive substance accommodating chambers will be in the range of 1 mm to 3 mm.

In general, it is envisaged that where the micro-needle devices are provided with a puncturing member for puncturing the first membrane, the penetrating tip of the puncturing members will terminate within the cavities within a plane defined by the first major surface of the first major surface of the micro-needle support layer, and typically, will terminate at a distance in the range of 200 microns to 500 microns from the plane defined by the first major surface thereof.

The number of micro-needles provided on the micro-needle support layer will vary depending on the treatment regime to be provided by the micro-needle device. However, typically, the micro-needle device may comprise anywhere from 6 micro-needles to 100 micro-needles, and while in general, the array of micro-needles may define a square, the array of micro-needles may define a rectangle, a circle, a hexagon or an octagon or the like, whereby the micro-needles would be contained within an area defined by a square, a rectangle, a circle, a hexagon or an octagon.

While the drive substance accommodating chambers have been described as extending through the drive substance accommodating layer from the first major surface to the second major surface, it is envisaged that in certain cases the drive substance accommodating chambers may not extend completely through the drive substance accommodating layer. For example, the drive substance accommodating chambers may extend into the drive substance accommodating layer from the first major surface thereof and terminate short of the second major surface thereof. In which case, it is envisaged that the activating means for activating the drive substance in the drive substance accommodating chambers would be located on the second major surface of the drive substance accommodating layer adjacent the corresponding drive substance accommodating chambers. Alternatively, the activating means may be located in the base of each drive substance accommodating chamber.

The invention claimed is:

1. A micro-needle device for transferring a substance between the device and a subject, the device comprising:
   a first layer having a pair of opposite major surfaces and at least one storage chamber extending into the first layer from at least one of the major surfaces thereof,
   a second layer comprising at least one micro-needle extending therefrom, having a first major surface, at least one communicating opening extending through the second layer from the first major surface thereof communicating with the at least one micro-needle,
   a membrane located between the first major surface of the second layer and the major surface of the first layer from which the at least one storage chamber therein extends, and
   a seal effecting projecting element extending from one of the first major surface of the second layer and the major surface of the first layer, from which the at least one storage chamber extends into the first layer, the seal effecting projecting element being of annular configuration, extending around a corresponding one of the at least one storage chamber and the at least one communicating opening and engaging the membrane and effecting a seal between the membrane and the first major surface of the second layer and the major surface of the first layer, from which the at least one storage chamber extends into the first layer, adjacent the corresponding one of the at least one storage chamber and the at least one communicating opening.

2. A micro-needle device as claimed in claim 1 in which the seal effecting projecting element terminates in a membrane abutting surface.

3. A micro-needle device as claimed in claim 1 in which the seal effecting projecting element extending from the major surface of one of the first layer and the second layer comprises one of a pair of interengageable complementary seal effecting formations for engaging the membrane therebetween, the other one of the seal effecting formations being formed by a seal effecting recess formed into the major surface of the other one of the first layer and the second layer and extending around the corresponding one of the at least one storage chamber and the at least one communicating opening.

4. A micro-needle device as claimed in claim 3 in which the seal effecting recess extends into the one of the at least one storage chamber and the at least one communicating opening adjacent the corresponding major surface thereof.

5. A micro-needle device as claimed in claim 3 in which the seal effecting recess tapers inwardly from the major surface of the corresponding one of the first layer and the second layer.

6. A micro-needle device as claimed in claim 3 in which the seal effecting projecting element tapers inwardly from the major surface of the corresponding one of the first layer and second layer.

7. A micro-needle device as claimed in claim 6 in which the seal effecting projecting element tapers inwardly from the corresponding major surface of the corresponding one of the first layer and the second layer at an angle corresponding to the angle at which the corresponding seal effecting recess tapers inwardly from the corresponding major surface of the other one of the first layer and the second layer.

8. A micro-needle device as claimed in claim 1 in which a gasket is located between the membrane and the adjacent major surface of the one of the first layer and the second layer with which a seal is to be effected, so that a corresponding one of the seal effecting projecting elements extending from the other of the major surfaces adjacent the membrane which engages the membrane urges the gasket into engagement with the major surface of the one of the first layer and the second layer against which the gasket is adjacent through the membrane, the gasket having at least one opening therethrough for communicating with a corresponding one of the at least one storage chamber in the first layer and the at least one communicating opening in the second layer.

9. A micro-needle device as claimed in claim 8 in which the gasket is recessed into the adjacent major surface of the corresponding one of the first and second layers with which a seal is to be effected.

10. A micro-needle device as claimed in claim 1 in which the membrane located between the first layer and the second layer comprises a first membrane of a burstable material, so that when burst communication is established between the at least one storage chamber in the first layer and a corresponding one of the at least one communicating opening of the second layer for accommodating a substance between the at least one storage chamber and a corresponding one of the at least one micro-needle of the second layer.

11. A micro-needle device as claimed in claim 10 in which the first membrane is burstable adjacent the at least one storage chamber in response to one of a positive pressure and a negative pressure being applied thereto from the storage chamber.

12. A micro-needle device as claimed in claim 11 in which the first membrane is burstable adjacent the at least one storage chamber in response to a positive pressure being applied thereto from the storage chamber.

13. A micro-needle device as claimed in claim 10 in which the first membrane is selectively burstable adjacent the respective storage chambers.

14. A micro-needle device as claimed in claim 1 in which a plurality of storage chambers are provided in the first layer.

15. A micro-needle device as claimed in claim 1 in which the seal effecting projecting element extends from the major surface of the first layer.

16. A micro-needle device as claimed in claim 1 in which the seal effecting projecting element extends from the first major surface of the second layer.

17. A micro-needle device as claimed in claim 1 in which the second layer defines a second major surface opposite the first major surface, and the at least one micro-needle extends from the second major surface of the second layer, and a communicating bore extends through the second layer from the at least one communicating opening in the first major surface thereof to the corresponding at least one micro-needle.

18. A micro-needle device for transferring a substance between the device and a subject, the device comprising:

a first layer having a pair of opposite major surfaces and at least one storage chamber extending into the first layer from at least one of the major surfaces thereof, a second layer having a first major surface, and at least one drive substance accommodating chamber therein, and at least one communicating opening extending through the first major surface thereof communicating with the at least one drive substance accommodating chamber, a membrane located between the first major surface of the second layer and the major surface of the first layer from which the at least one storage chamber therein extends, and a seal effecting projecting element extending from one of the first major surface of the second layer and the major surface of the first layer, from which the at least one storage chamber extends into the first layer, the seal effecting projecting element being of annular configuration, extending around a corresponding one of the at least one storage chamber and the at least one communicating opening and engaging the membrane and effecting a seal between the membrane and the first major surface of the second layer and the major surface of the first layer, from which the at least one storage chamber extends into the first layer, adjacent the corresponding one of the at least one storage chamber and the at least one communicating opening.

19. A micro-needle device as claimed in claim 18 in which the membrane located between the first layer and the second layer comprises a second membrane of a stretchable material, the communicating opening to the at least one drive substance accommodating chamber being defined by a corresponding open mouth to the drive substance accommodating chamber formed in the first major surface of the second layer.

20. A micro-needle device as claimed in claim 19 in which the second membrane is adapted to stretch into the at least one storage chamber in the first layer corresponding to the at least one drive substance chamber in the second layer.

* * * * *